(12) United States Patent
Duval

(10) Patent No.: US 12,357,850 B2
(45) Date of Patent: Jul. 15, 2025

(54) DEVICES FOR PREVENTING INHALATION OF, EXPOSURE TO, AIRBORNE MATERIAL

(71) Applicant: Landon Duval, San Clemente, CA (US)

(72) Inventor: Landon Duval, San Clemente, CA (US)

( * ) Notice: Subject to any disclaimer, the term of this patent is extended or adjusted under 35 U.S.C. 154(b) by 849 days.

(21) Appl. No.: 17/303,459

(22) Filed: May 28, 2021

(65) Prior Publication Data

US 2021/0370108 A1 Dec. 2, 2021

Related U.S. Application Data

(60) Provisional application No. 63/037,958, filed on Jun. 11, 2020, provisional application No. 63/032,907, filed on Jun. 1, 2020.

(51) Int. Cl.
*A62B 23/02* (2006.01)
*A41D 13/11* (2006.01)
(Continued)

(52) U.S. Cl.
CPC ........ *A62B 23/025* (2013.01); *A41D 13/1161* (2013.01); *A61L 9/20* (2013.01);
(Continued)

(58) Field of Classification Search
CPC ...... A41D 13/1161; A41D 13/11–1192; A61L 9/20; A61L 2209/12; A61L 2209/14;
(Continued)

(56) References Cited

U.S. PATENT DOCUMENTS

| 715,052 A | 12/1902 | Goodwin |
|---|---|---|
| 1,044,698 A | 11/1912 | Sideman |

(Continued)

FOREIGN PATENT DOCUMENTS

| CN | 204888804 | 12/2015 |
|---|---|---|
| EM | EU 007826367-0014 | 7/2020 |

(Continued)

OTHER PUBLICATIONS

Lu et al., "Transparent air filter for high-efficiency $PM_{2.5}$ capture", Nature Communications, Jan. 6, 2015, pp. 1-9.
(Continued)

*Primary Examiner* — Rachel T Sippel
(74) *Attorney, Agent, or Firm* — KNOBBE, MARTENS, OLSON & BEAR LLP

(57) ABSTRACT

A protection device for preventing exposure to undesired airborne material. The device including a filter assembly having a filter, and a proximal and a distal layer configured to hold the filter sandwiched between the proximal layer and the distal layer, a one-way valve positioned in the filter assembly and coupled to the proximal layer of the filter assembly, and a seal positioned along a peripheral edge of the filter assembly, the filter assembly and the seal defining a first safety compartment for enclosing a user's mouth and nose. The device can include an eye shield assembly having a skirt extending from the filter assembly and positioned distal to the seal, an optically transparent eye shield coupled to the skirt to form a continuous surface from the filter assembly to a top portion of the eye shield, and a frame coupled to the frame assembly and eye shield assembly.

18 Claims, 28 Drawing Sheets

(51) Int. Cl.
    *A61F 9/02* (2006.01)
    *A61L 9/20* (2006.01)
    *A62B 18/08* (2006.01)
    *A62B 18/10* (2006.01)
    *H04R 1/08* (2006.01)
    *H04R 1/10* (2006.01)

(52) U.S. Cl.
    CPC ............ *A62B 18/084* (2013.01); *A62B 18/10* (2013.01); *H04R 1/08* (2013.01); *H04R 1/105* (2013.01); *A61F 9/029* (2013.01); *A61L 2209/12* (2013.01); *A61L 2209/14* (2013.01); *A61L 2209/15* (2013.01)

(58) Field of Classification Search
    CPC ..... A61L 2209/15; A62B 7/10; A62B 18/082; A62B 23/02–025; A62B 23/00–025; A62B 18/00; A62B 18/02–025; A62B 18/08–084; A62B 18/088–10; A62B 7/00; A62B 9/00; A62B 9/02; A62B 9/04; H04R 1/08; H04R 1/105; A61F 9/029
    USPC .................................................. 128/203.13
    See application file for complete search history.

(56) References Cited

U.S. PATENT DOCUMENTS

| | | | |
|---|---|---|---|
| 1,199,529 A | 9/1916 | Collman | |
| 1,298,347 A | 3/1919 | Jordan | |
| D93,702 S | 10/1934 | Campbell | |
| 2,081,779 A | 5/1937 | Titus | |
| 2,281,181 A | 4/1942 | Clarke | |
| 2,447,450 A | 8/1948 | Williams | |
| 2,389,102 A | 11/1948 | Williams | |
| 2,498,668 A | 2/1950 | James | |
| 2,753,762 A | 7/1956 | Doregelys | |
| 2,774,279 A | 12/1956 | Olson et al. | |
| 2,954,027 A | 9/1960 | Marasco | |
| 3,308,816 A | 3/1967 | Franklin et al. | |
| 3,333,585 A | 8/1967 | Barghini | |
| 3,850,168 A * | 11/1974 | Ferguson ............ | A62B 18/084 128/201.19 |
| 4,057,057 A * | 11/1977 | Backlund ............ | A62B 18/082 128/201.12 |
| 4,595,003 A * | 6/1986 | Shoemaker ............ | A62B 18/02 128/206.17 |
| 4,796,621 A * | 1/1989 | Barle ...................... | A61F 9/029 128/206.19 |
| 4,944,039 A | 7/1990 | Dietrich | |
| 5,012,805 A | 5/1991 | Muckerheide | |
| D319,111 S | 8/1991 | Sandel | |
| D323,570 S | 1/1992 | Jacobson | |
| D343,307 S | 1/1994 | Tennyson | |
| 5,406,944 A * | 4/1995 | Gazzara ............... | A62B 18/082 128/201.12 |
| 6,543,450 B1 * | 4/2003 | Flynn .................... | A62B 18/02 128/206.25 |
| 6,718,981 B2 | 4/2004 | Cardarelli | |
| 6,948,499 B2 | 9/2005 | Griesbach, III et al. | |
| D564,135 S | 3/2008 | Cherry | |
| D589,211 S | 3/2009 | Stevens | |
| 7,520,923 B2 | 4/2009 | Marcoon | |
| 7,802,572 B2 | 9/2010 | Hahne | |
| 7,836,887 B1 | 11/2010 | Kling | |
| 7,942,524 B2 | 5/2011 | Smith | |
| D657,052 S | 4/2012 | Amin | |
| 9,188,794 B2 | 11/2015 | Adal | |
| D746,439 S | 12/2015 | Steindorf | |
| 9,629,401 B2 | 4/2017 | Al Malki | |
| D820,434 S | 6/2018 | Bergman | |
| D821,568 S | 6/2018 | Nilsson | |
| D855,174 S | 7/2019 | Fofack | |
| D862,569 S | 10/2019 | Huang | |
| D868,960 S | 12/2019 | Tu | |
| D882,758 S | 4/2020 | Eitzman | |
| D885,559 S | 5/2020 | Gabriel | |
| D905,847 S | 12/2020 | Orman | |
| 10,888,130 B1 | 1/2021 | Naos | |
| 11,027,157 B1 | 6/2021 | Mortimer | |
| 11,206,880 B1 | 12/2021 | Naos | |
| D945,078 S | 3/2022 | Wu | |
| D949,327 S | 4/2022 | Park | |
| D961,857 S | 8/2022 | Oaks | |
| D962,421 S | 8/2022 | Kim | |
| 2004/0011363 A1 * | 1/2004 | Wiener .................. | A62B 18/10 128/206.17 |
| 2004/0211426 A1 * | 10/2004 | Lai ........................ | A61B 90/00 128/206.23 |
| 2005/0103344 A1 * | 5/2005 | Cheng .................. | A41D 13/1161 128/206.13 |
| 2006/0230485 A1 * | 10/2006 | Lee ...................... | A41D 13/1138 2/15 |
| 2007/0277829 A1 * | 12/2007 | Casewell ............... | A62B 18/10 128/206.24 |
| 2009/0126064 A1 | 5/2009 | Reaux | |
| 2009/0320849 A1 | 12/2009 | Biedermann | |
| 2010/0126504 A1 * | 5/2010 | Johnstone ............... | A61F 9/029 128/202.13 |
| 2013/0014316 A1 * | 1/2013 | Castro .................... | G02C 11/00 2/427 |
| 2015/0020815 A1 | 1/2015 | Gabriel | |
| 2015/0053206 A1 * | 2/2015 | Seppala ................. | A62B 18/10 128/206.17 |
| 2015/0314148 A1 | 11/2015 | Waterford | |
| 2016/0038775 A1 * | 2/2016 | O'Neal, Jr. ............ | A62B 18/02 128/206.12 |
| 2016/0324228 A1 * | 11/2016 | Ito ...................... | A41D 13/1161 |
| 2016/0332008 A1 * | 11/2016 | McAndrews ......... | A62B 18/025 |
| 2017/0014304 A1 * | 1/2017 | Tarumi ..................... | A61N 2/06 |
| 2017/0065838 A1 * | 3/2017 | Bunge .................. | A62B 18/084 |
| 2017/0157436 A1 | 6/2017 | Hosmer | |
| 2018/0280738 A1 * | 10/2018 | Gabriel ............... | A62B 18/025 |
| 2019/0022434 A1 * | 1/2019 | Sibuet .................. | A62B 25/005 |
| 2019/0133219 A1 * | 5/2019 | Shibata ............... | A41D 13/1138 |
| 2020/0261684 A1 * | 8/2020 | Fyke ..................... | A62B 18/08 |
| 2020/0359717 A1 | 11/2020 | Han | |
| 2020/0368068 A1 * | 11/2020 | Wu ...................... | A41D 13/1184 |
| 2021/0307413 A1 | 10/2021 | Scalisi | |
| 2021/0330851 A1 * | 10/2021 | Bell ..................... | A41D 13/1192 |
| 2021/0353971 A1 * | 11/2021 | Lane .................... | A62B 18/025 |
| 2021/0370108 A1 | 12/2021 | Duval | |
| 2021/0393140 A1 | 12/2021 | Rein | |
| 2021/0401084 A1 | 12/2021 | Lamoncha | |
| 2022/0087333 A1 | 3/2022 | Craigwell | |
| 2022/0184429 A1 | 6/2022 | Lee | |
| 2022/0305302 A1 * | 9/2022 | Hall ..................... | A62B 18/006 |
| 2022/0104561 A1 | 11/2022 | Meyer | |
| 2024/0315876 A1 | 9/2024 | Duval | |

FOREIGN PATENT DOCUMENTS

| | | |
|---|---|---|
| EM | EU 008111538-0001 | 8/2020 |
| EM | EU 008169916-0002 | 9/2020 |
| EM | EU 008537203-0002 | 5/2021 |
| GB | 9008173280-0002 | 9/2020 |
| JP | 2008-110184 | 5/2008 |
| WO | WO 2018/220516 | 12/2018 |

OTHER PUBLICATIONS

"3M: Particulate Respirator 8211". Found online at Amazon.com. Sep. 8, 2022. Reference dated|Sep. 1, 2004. Retrieved from https://www.amazon.com/3 M-Particulate-Respirator-8211-N 95/dp/B008 MCV2 Ku.

"Beiyoyo: Durable Clear Face Mask". Found online at Amazon.com. Sep. 7, 2022. Reference dated Nov. 18, 2020. Retrieved from https://www.amazon.com/BeiYoYo-Reusable-Transparent-Protection-Expression , Breathable/dp/B08LH3TP8J/.

(56) References Cited

OTHER PUBLICATIONS

"G&F: 9116 N95 Particulate Respirator". Found online at Amazon.com. Aug. 11, 2022. Reference dated Sep. 21, 2015. Retrieved from https://www.amazon.com/9116-Particulate-Respirator-Valve-Pieces/dp/B016211BPE.

"Honeywell: Safety Light Gray Dual Layer Face Cover". Found online at Amazon.com. Aug. 11, 2022.Reference dated Dec. 11, 2020. Retrieved from https://www.amazon.com/Honeywell-Light-Replaceable-Fiters-RWS-50107/dp/B08QDRC6WQ/.

International Search Report and Written Opinion issued in application No. PCT/US2021/034822, dated Sep. 13, 2021.

\* cited by examiner

DEVICES FOR PREVENTING INHALATION OF, EXPOSURE TO, AIRBORNE MATERIAL

INCORPORATION BY REFERENCE TO ANY PRIORITY APPLICATIONS

Any and all applications for which a foreign or domestic priority claim is identified in the Application Data Sheet as filed with the present application are hereby incorporated by reference under 37 CFR 1.57. This application claims the benefit of U.S. Provisional Patent Application Nos. 63/037,958 (filed Jun. 11, 2020) and 63/032,907 (filed Jun. 1, 2020), and the content of each of these disclosure is hereby incorporated by reference in its entirety.

BACKGROUND

Field

The present disclosure relates to protecting a user from airborne material, and specifically to devices for preventing inhalation of, and expose to, undesired airborne material, including dust, pollen, and virus-laden aerosol.

Description of the Related Art

In many situations, a user desires to limit the amount and types of materials or particles that are inhaled, and limit the exposure of their eyes to such material. For example, in during cleaning, construction, or in medical environments. Current dust masks and the like can be difficult to put on and take off, and can take both hands to do so. Typical masks do not form an airtight seal around a user's mouth and nose, and do not form an airtight seal around a user's eyes. When a mask is worn, a person that the mask where is talking to cannot see the mask wearers mouth which may make communication more difficult and less personal. In addition, it can be difficult to use a telephone while wearing a mask or a face shield. Due to these challenges, people may decide not to wear protective devices in environments where they should to protect their health and safety, and ultimately the health and safety of others as well. Accordingly, it would be advantageous to address these and other disadvantages in new devices that protect a user from airborne material.

SUMMARY

Several innovations are disclosed herein, each having multiple aspects that can be included in various embodiments of the innovations. Some of the innovations are protection devices that have features for protecting a user from inhalation of undesired airborne material, and can have features for protecting a user's eyes from exposure to undesired airborne material. Other innovations relate to devices for easily attaching a filter, or filter assembly, to the head of a user.

For example, one innovation is a protective device, the protective device including a filter assembly having a proximal side and a distal side, the proximal side positioned closest to a user when the protective device is worn by the user (on the user's head), and the distal side positioned facing away from the user. The filter assembly comprises a filter; a proximal layer and a distal layer where the proximal layer is positioned closer to the user than the distal layer, the proximal layer and the distal layer each having a plurality of perforations that allow air to pass through. The filter assembly is configured to hold the filter between the proximal layer and the distal layer. The device also includes a one-way valve positioned in a center portion of the filter assembly and coupled to the proximal layer of the filter assembly, the valve configured to allow air to pass through the valve from the proximal side of the filter assembly to the distal side of the filter assembly, a seal positioned along a peripheral edge of the filter assembly, the filter assembly and the seal defining a first safety compartment for enclosing a user's mouth and nose, and a frame assembly coupled to the filter assembly and structured to attach the protection device to the head of a user. The frame assembly can include a left temple arm having a proximal end coupled to the filter assembly, a right temple arm having a proximal end coupled to the filter assembly, a left temple arm brace coupled to the left temple arm and extending towards a lower portion of the filter assembly and coupled to the lower portion of the filter assembly, and a right temple arm brace coupled to the left temple arm and extending towards a lower portion of the filter assembly and coupled to the lower portion of the filter assembly.

Various embodiments of such devices can include one or more other aspects. In some embodiments, the device includes a left ear support on a distal end of the left temple arm distal and a right ear support on a distal end of the right temple arm, the left and right ear supports structured to extend around a portion of the user's ears to hold the protection device securely on the user. In some embodiments, the device further comprises a communication circuit, which may include a microphone which may be positioned on the valve. The communication circuit can include a battery, and/or at least one speaker. In some embodiments, the protection device further comprises left and right ear supports, and the at least one speaker is positioned in one or both of the left and right ear supports. In some embodiments, the communications circuit is configured to communicate with another device via a wired or wireless connection. In some embodiments, the protection device further comprises left and right ear supports, wherein at least a portion of the communication circuit is positioned in the left and right ear supports. In some embodiments, the filter includes a proximal surface and a distal surface, and wherein the protection device further comprises UV-C light emitting diode (LED) positioned to emit UV-C radiation on a portion of the distal surface of the filter. In some embodiments, the filter includes a proximal surface and a distal surface, and wherein the protection device further comprises one or more light emitting diodes (LED's) that emit ultraviolet radiation. For example, the device can include one or more UV-C LED's positioned to emit UV-C radiation on a portion of the distal surface of the filter. In some embodiments including the examples illustrated in FIGS. 1-27, the devices can include UV-C LED's that emit light on the distal surface of the filter and/or the distal layer of the filter assembly, for example, to the left and right side of a one-way valve. UV-C LED's are a class of LED's that emit UV-C radiation, which refers to a class of ultraviolet energy wavelengths that have a unique ability to kill viruses, bacteria, mold, and other pathogens. In some embodiments, two UV-C LED's are a first set of LED's and are positioned on, or coupled to, the one-way valve. Such devices can include one or more other UV-C LED's, or sets of UV-C LED's. For example, the other UV-C LED's can be coupled to a side of the one-way valve, the UV-C LED's positioned to emit light on the filter assembly on an outer surface of the distal layer of the filter assembly, or emit light within the filter assembly between the proximal layer and the distal layer. In some embodiments, the proximal and distal layer each comprises a plurality of openings arranged in a pattern. In some embodiments, the distal layer and the filter are removably attachable to the filter assembly, the one-way valve is coupled to the proximal layer of the filter assembly, and the filter incudes an opening shaped and sized to fit closely around the one-way valve when the filter is sandwiched between the distal layer and the proximal layer of the filter assembly. In some embodiments, the distal layer and the proximal layer include corresponding and aligned fasteners positioned along peripheral edges of the distal and proximal layers for coupling the distal layer to the proximal layer. The device can include a safety strap connected to the left temple arm and the right temple arm for positioning behind the head of a user. In some embodiments, the filter assembly comprises a transparent material.

Another innovation includes a protection device, comprising a filter assembly having a proximal side for positioning near a user's face and a distal side, the filter assembly comprising: a filter; a proximal layer and a distal layer, the proximal layer and the distal layer each having a plurality of perforations that allow air to pass through, the file assembly configured to hold the filter between the proximal layer and the distal layer; a one-way valve positioned in a center portion of the filter assembly and coupled to the proximal layer of the filter assembly, the valve configured to allow air to pass through the valve from the proximal side of the filter assembly to the distal side of the filter assembly; a seal positioned along a peripheral edge of the filter assembly, the filter assembly and the seal defining a first safety compartment for enclosing a user's mouth and nose; an eye shield assembly having a proximal side and a distal side, and the eye shield assembly forming an upper portion of the protection device, the eye shield assembly comprising a skirt extending from the filter assembly and positioned distal to the seal, the skirt comprising a semi-rigid or rigid material; an optically transparent eye shield coupled to the skirt to form a continuous surface from the filter assembly to a top portion of the eye shield; and a frame assembly coupled to the filter assembly and structured to attach the protection device to the head of a user. The frame assembly can include a left temple arm having a proximal end coupled to the filter assembly, a right temple arm having a proximal end coupled to the filter assembly, a left temple arm brace coupled to the left temple arm and extending towards a lower portion of the filter assembly and coupled to the filter assembly, and a right temple arm brace coupled to the left temple arm and extending towards a lower portion of the filter assembly and coupled to the filter assembly. Such devices can include any of the features described in the previously described innovation of a protective device. In some embodiments, the filter assembly and the eye shield assembly including the skirt can be made from a transparent material such that the filter assembly and the eye shield assembly are transparent.

Another innovation includes a protection device including a filter assembly having a proximal side for positioning near a user's face and a distal side, the filter assembly comprising: a filter; a proximal layer and a distal layer, the proximal layer and the distal layer each having a plurality of perforations that allow air to pass through, the file assembly configured to hold the filter between the proximal layer and the distal layer; a one-way valve positioned in a center portion of the filter assembly and coupled to the proximal layer of the filter assembly, the valve configured to allow air to pass through the valve from the proximal side of the filter assembly to the distal side of the filter assembly; a seal positioned along a peripheral edge of the filter assembly, the filter assembly and the seal defining a first safety compartment for enclosing a user's mouth and nose; an eye shield assembly having a proximal side and a distal side, and the eye shield assembly forming an upper portion of the protection device, the eye shield assembly comprising a skirt extending from the filter assembly and positioned distal to the seal, the skirt comprising a semi-rigid or rigid material; and an optically transparent eye shield coupled to the skirt to form a continuous surface from the filter assembly to a top portion of the eye shield, wherein the seal is further positioned along a peripheral edge of the eye shield assembly, the eye shield assembly and the seal defining a second safety compartment for enclosing a user's eyes, wherein the first safety compartment is separate from the second safety compartment when worn by a user such that air cannot flow between the first safety compartment and the second safety compartment; and a frame assembly coupled to the filter assembly and structured to attach the protection device to the head of a user. The frame assembly can include a left temple arm having a proximal end coupled to the filter assembly; a right temple arm having a proximal end coupled to the filter assembly; a left temple arm brace coupled to the left temple arm and extending towards a lower portion of the filter assembly and coupled to the filter assembly; and a right temple arm brace coupled to the left temple arm and extending towards a lower portion of the filter assembly and coupled to the filter assembly. Such protection devices can include one or more additional features, for example, any of the features described herein for protection devices, or other features.

Another innovation includes a device comprising a frame for holding a filter, the frame including a first temple arm configured to be coupled to a portion of a filter; and a second temple arm configured to be coupled to a portion of the filter. In some embodiments, the first temple arm comprises a first fastener positioned on a proximal end of the temple arm, and wherein the second temple arm comprises a second fastener positioned on a proximal end of the second temple arm. In some embodiments, the frame further includes a first support having a first end coupled to the first temple arm and a second end configured to be coupled to a portion of the filter; and a second support having a first end coupled to the second temple arm and a second end configured to be coupled to the filter. In some embodiments, the first support comprises a third fastener positioned on the second end of the first support, and wherein the second support comprises a fourth fastener positioned on the second end of the second support. In some embodiments, wherein at least one fastener comprises a clamp. In some embodiments, the clamp comprises a spring. In some embodiments, the at least one fastener comprises Velcro. In some embodiments, the at least one fastener comprises an adhesive. In some embodiments, the at least one fastener comprises a staple. In some embodiments, at least one fastener comprises a snap. In some embodiments, the at least one fastener comprises a button. In some embodiments, the frame comprises hard plastic or an elastomeric material. In some embodiments, at least one of the first or second temple arms comprises a curved portion configured to be positioned behind the ear of a user. In some embodiments, at least one of the first or second temple arms comprises an earpiece configured to produce sound. In some embodiments, the device further includes a wired or wireless receiver coupled to the ear piece. In some embodiments, the first and second supports comprise a stretchable material. In some embodiments, the frame comprises a fastener configured to be coupled to a corresponding fastener on a filter. The device can further comprise a filter.

Another innovation includes a method of preventing inhalation of undesired material, the method comprising providing a device having a frame for holding a filter, the frame including a first temple arm having a fastener configured to be coupled to a portion of a filter; a second temple arm having a fastener configured to be coupled to a portion of the filter; a first support having a first end coupled to the first temple arm and a second end having a fastener configured to be coupled to a portion of the filter, and a second support having a first end coupled to the second temple arm and a second end having a fastener configured to be coupled to a portion of the filter; coupling a filter to the first temple arm, the second temple arm, the first support, and the second support; and positioning the device on the head of a user such that the filter covers the user's nose and mouth, and the first temple arm is positioned adjacent to the user's right temple and the second temple arm is positioned adjacent to the user's left temple.

Another innovation includes a device, comprising a frame for holding a filter, the frame including a first temple arm having a proximal end and a distal end, the first temple arm including a fastener positioned on the proximal end for coupling the first temple arm to a filter, the distal end structured to be positioned alongside a temple of a user wearing the device; a second temple arm having a proximal end and a distal end, the second temple arm including a fastener positioned on the proximal end for coupling the second temple arm to a filter, the distal end structured to be positioned alongside a temple of a user wearing the device; and a first support having a first end coupled to the first temple arm and a second end including a fastener configured for coupling the first support to a portion of the filter; and a second support having a first end coupled to the second temple arm and a second end including a fastener configured for coupling the second support to a portion of the filter. In some embodiments, the fasteners are releasably attachable to the filter. In some embodiments, the device further includes a filter coupled to the first temple arm, the second temple arm, the first support, and the second support. In some embodiments, the frame further comprises a bridge structure connecting the proximal end of the first temple arm to the proximal end of the second temple arm. In some embodiments, the frame further comprises a lower member coupled to the second end of the first support and the second end of the second support. In some embodiments, the frame further comprises a lower member coupled to the second end of the first support and the second end of the second support; a first side member coupled to the proximal end of the first temple arm and coupled to the lower end of the first support; and a second side member coupled to the proximal end of the second temple arm and coupled to the lower end of the second support.

BRIEF DESCRIPTION OF THE DRAWINGS

The features and advantages of the embodiments described herein will become more fully apparent from the following description and appended claims, taken in conjunction with the accompanying drawings. These drawings depict only certain embodiments in accordance with the disclosure and are not to be considered limiting of its scope. In the drawings, similar reference numbers or symbols typically identify similar components, unless context dictates otherwise. In some instances, the drawings may not be drawn to scale.

DETAILED DESCRIPTION

Figure 1:
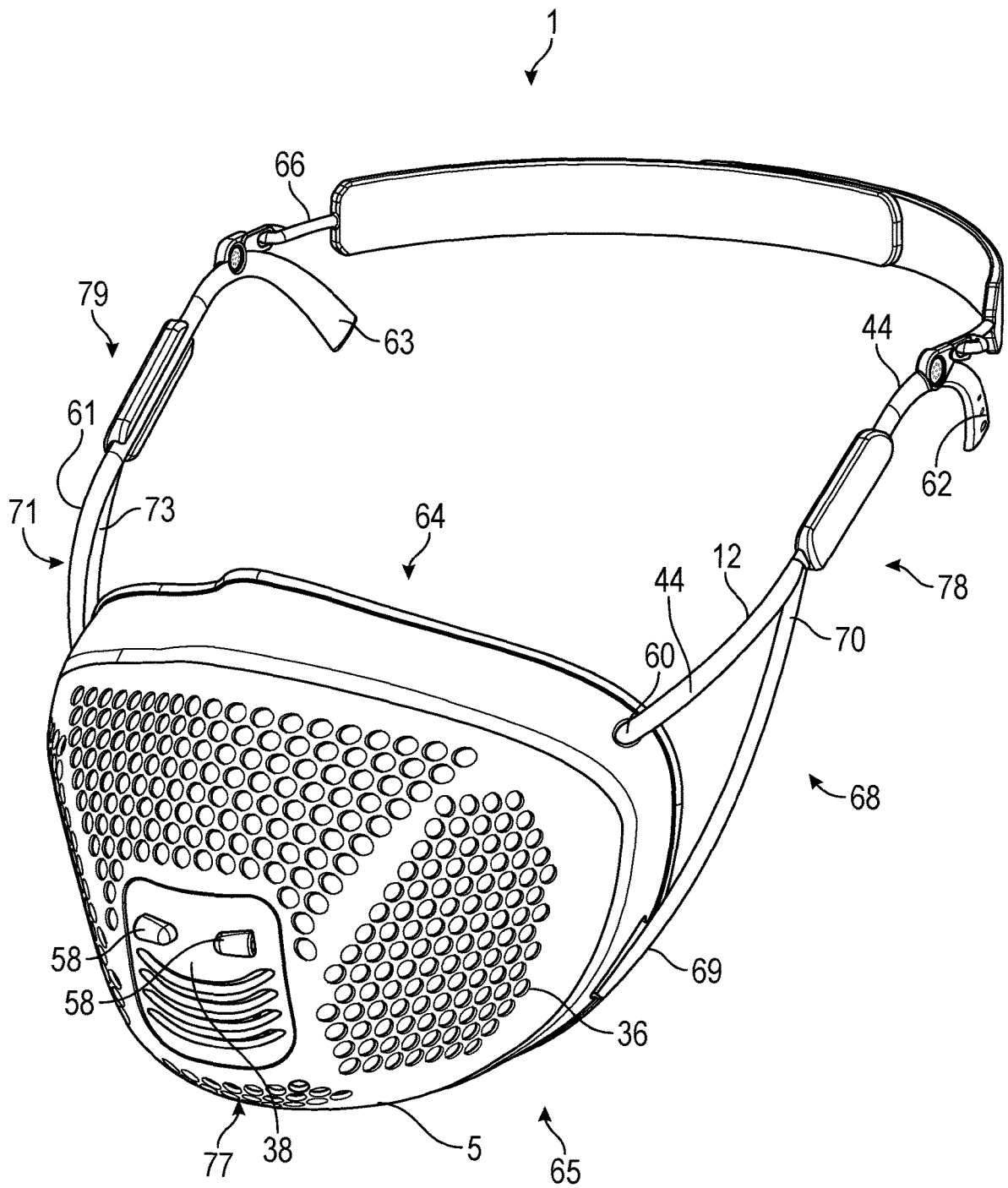
FIG. 1 is a front perspective view of an example of a first embodiment of a protection device having a filter assembly that is structured to cover a user's nose and mouth and to form a sealed compartment that encloses the user's nose and mouth, where in various examples the protective device can also include one or more other features, including for example, a microphone, earpieces, and/or other communication circuits, and UV-C light emitting diodes (LEDs).

Examples and embodiments of a protection device ("device") for preventing inhalation of undesired airborne materials, substances, dust, pollen, and virus-laden aerosol (all referred to as "material" for ease of description), each device having several aspects (features), no single aspect of which is solely responsible for its desirable attributes. Without limiting the scope of the claims that follow, some of these aspects are described below. The drawings referred to illustrate certain features that can be included on such devices. In some examples, for clarity of illustration, not all of the features of a particular device are necessarily included in a particular figure. Various illustrated or described devices also have additional features, including features that are illustrated or described elsewhere herein. Illustrations in the drawing sheets presented herein are examples only and should not be taken as limiting.

Masks, respirators, and shields are used to protect a user from exposure to unwanted material. Although such devices may be used in hazardous environments (e.g., medical, construction, etc.) they may not provide the needed protection to fully isolate the mouth and nose such that only filtered air is inhaled. Also, they may not protect a user's eyes, or inadequately protect a user's eyes. When a mask and eye shield are worn separately, there is a risk of exposure in the space between these devices. Also, because the eyes and an eye shield are not fully isolated from the nose and mouth, fogging of the eye shield can occur. In addition, as user's are wearing protection devices for long periods of time, communication (e.g., by phone) can be awkward, difficult, or impossible, depending on the device. Most protection devices offer only passive protection (a barrier). In some instances, the level of protection can be increased if active protection is employed (e.g., against virus). Protection devices described herein include features to address these issues and provide other advantages as well, for example, higher comfort, easy use and may have cost advantages compared to other protection devices that complete isolation of a user's eyes, nose and mouth. Such devices are re-usable, where only the filter needs to be disposed of regularly thus decreasing waste, and in particular hazardous waste. Some of these protection devices can include active systems for a higher level of protection from viruses, and can include communication features so the devices do not need to be removed for communication.

Figure 26:
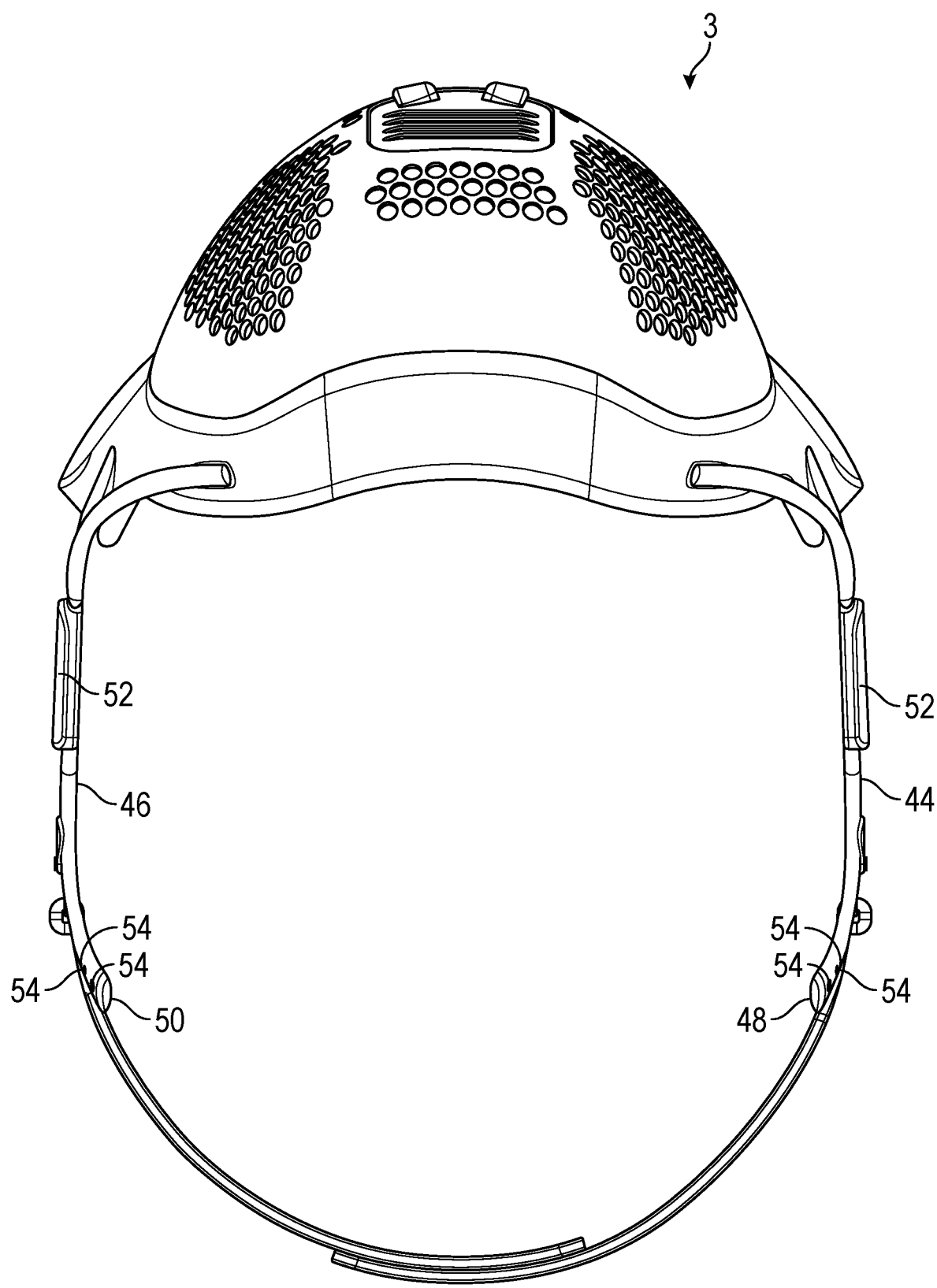
FIG. 26 is a bottom view of the embodiment of the protection device illustrated in FIG. 19.
Figure 27:
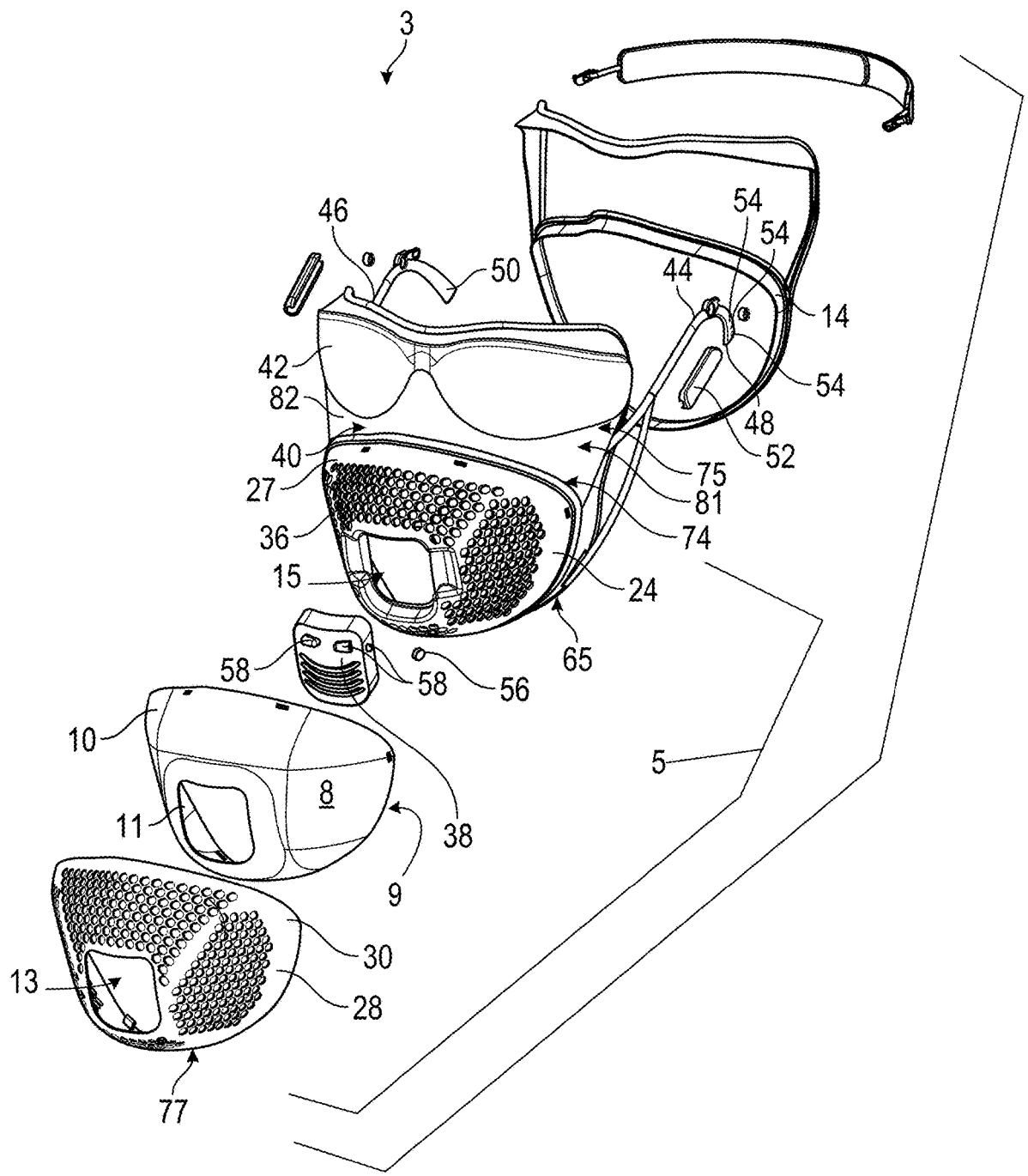
FIG. 27 is an exploded view of an example of the embodiment of the protection device illustrated in FIG. 19.
Figure 28:
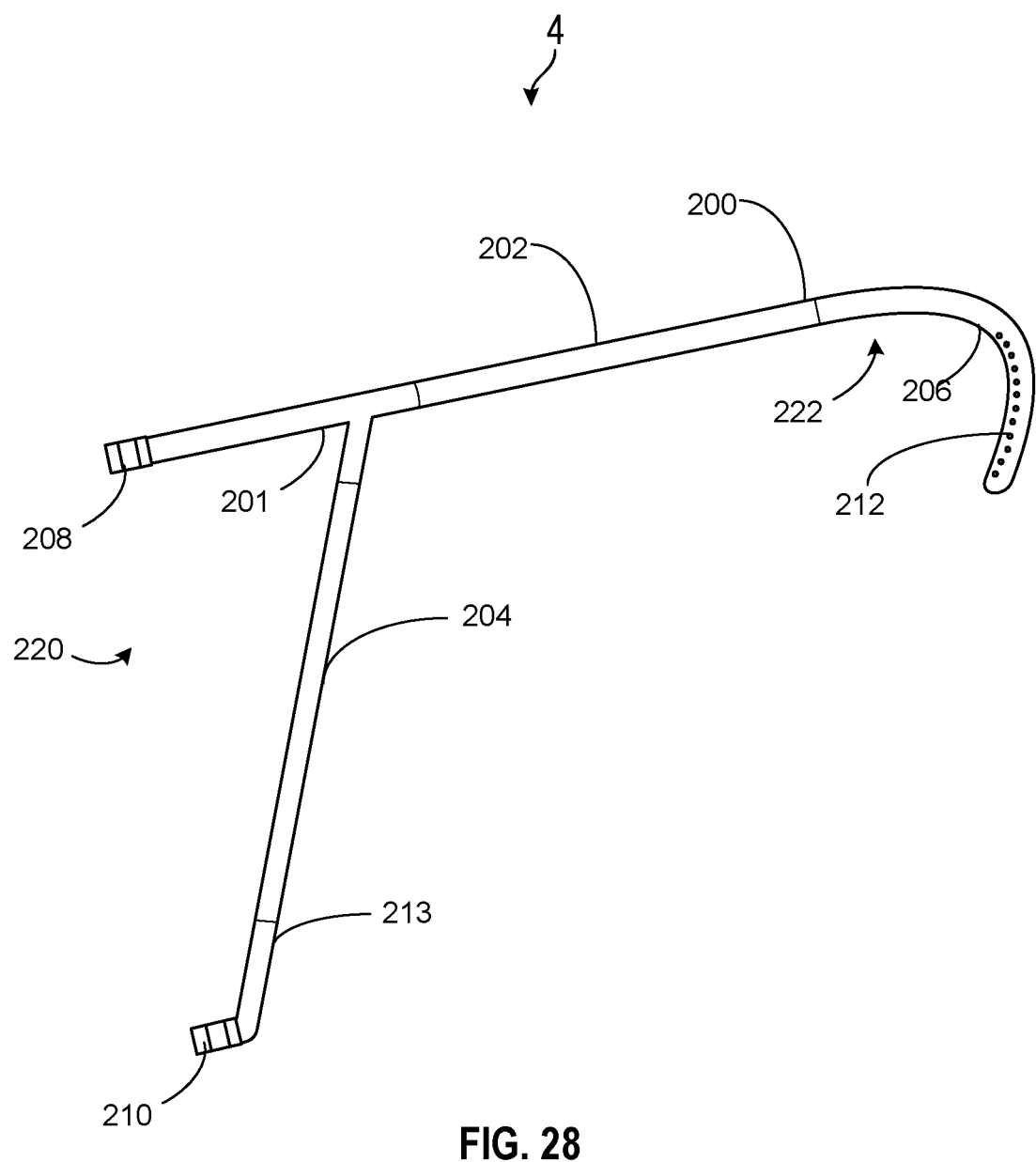
FIG. 28 illustrates an example of a side view of an arm assembly of a device that is configured to be coupled to a filter (or filter assembly) for attaching the filter to a user's face.

Examples of several embodiments of protection devices are described herein. FIGS. 1-9 show an example of a first embodiment of a protection device structured to have a filter assembly that forms a safety compartment for positioning around a user's nose and mouth. FIGS. 10-18 show in example of a second embodiment that is also structured to have a filter assembly that forms a safety compartment around a user's nose and mouth, an eye shield, and additionally includes a skirt extending between the filter assembly and the eye shield. FIGS. 19-27 show an example of a third embodiment of a protection device that is also structured to have a filter assembly that forms a first safety compartment around a user's nose and mouth, an eye shield, and a skirt extending between the filter assembly and an eye shield, and a second safety compartment for positioning around a user's eyes. FIG. 28 illustrates a device having a frame that is configured to be attached to a filter to hold the filter on the face of a user, allowing the filter to be easily removed and put back on using one hand. Any of these devices can include one or more features that provide easier use and/or better protection. In various embodiments, one or more portions of the devices (e.g., a filter, filter assembly, frame, eye shield, valve, seal, strap and/or skirt) can be made from transparent material which makes the device less visible and intrusive. Also, a transparent (or nearly transparent) mouth covering portion can help facilitate communication, and be a necessity for lip-reading needs.

Certain protection devices disclosed herein are structured to form a first safety compartment that can be positioned around a user's mouth and nose, and seal tightly to a user's face. Air that enters the first safety compartment can only do so by passing through a filter contained in a filter assembly. The filter assembly can include a proximal layer and a distal layer that are configured to be removably attachable and hold a filter therebetween. That is, the filter is sandwiched between the proximal and the distal layer. The filter is removable and replaceable. Various filters can be used in a filter assembly and may be selected based on the environment in which the device will be used (e.g., medical, construction, outside, home use, etc.). The proximal layer and the distal layer can include corresponding and aligned fasteners positioned along the edges of the proximal and distal layers that allow the proximal and distal layers to be connected and disconnected, for example, to change or replace a filter.

Certain protection devices disclosed herein are structured to form a second safety compartment that can be positioned around a user's eyes, preventing the eyes from being exposed to any unwanted material. The second safety compartment is separate from the first safety compartment such that air in one of these safety compartments does not communicate to the other safety department. That is, when the protection device is worn by a user, the first safety compartment is a separate sealed compartment from the second safety compartment.

The devices described herein can include features that address issues with current protection devices. For example, a device can have a communication circuit incorporated into its structure or attached thereon. The communication circuit can include a microphone, speakers and wired or wireless (e.g., Bluetooth) communication channels. In some embodiments, a portion of the communication circuit (e.g., speakers, receiver or transmitter circuits) are on an ear support portion of a temple arm such that when the device is worn the communication circuit is positioned at the back side of the user's ear such that the weight of the communication circuit (even though relatively light) helps to hold the ear support on the user's ear.

Figure 2:
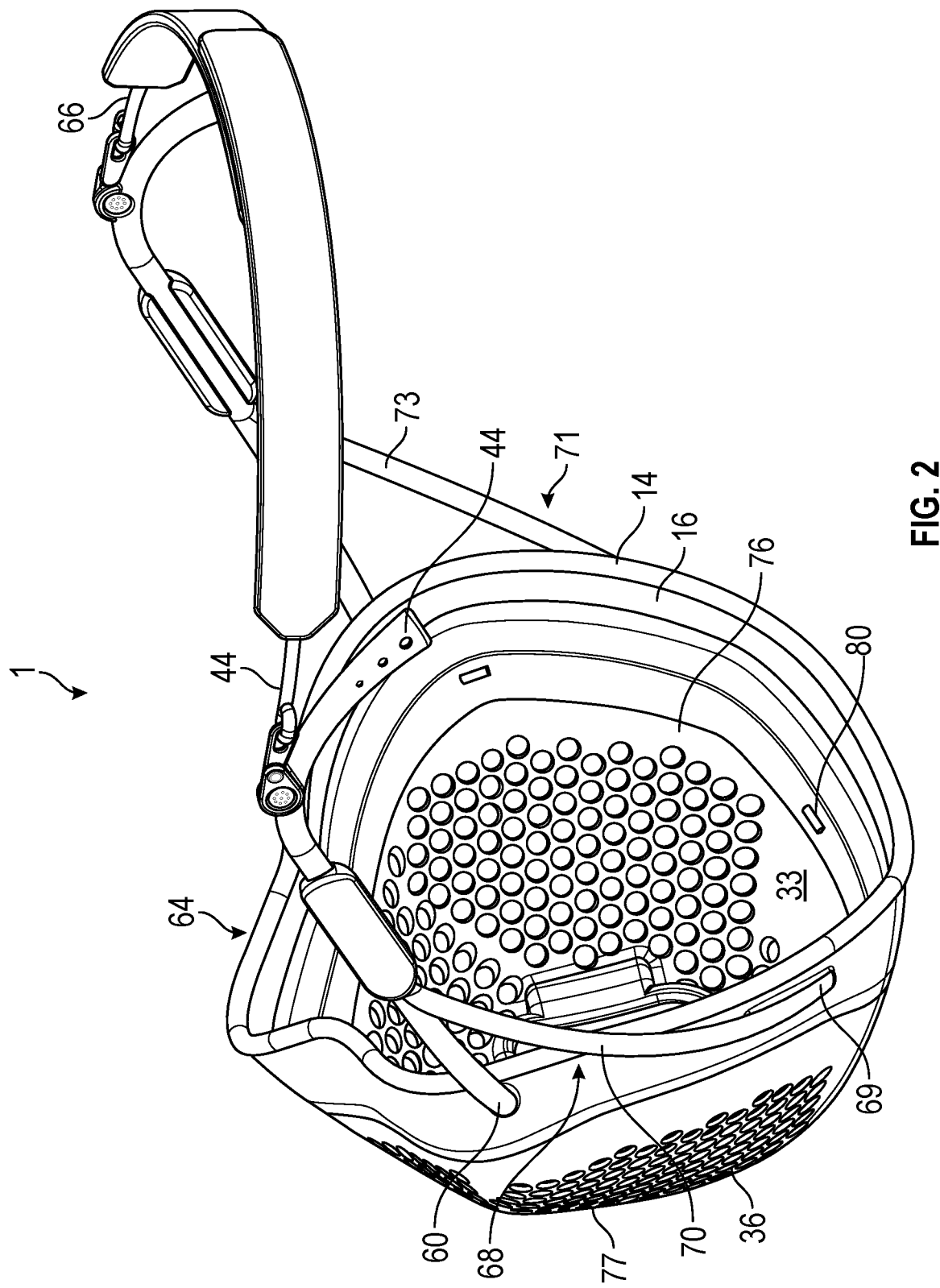
FIG. 2 is a back perspective view of the protection device illustrated in FIG. 1.
Figure 3:
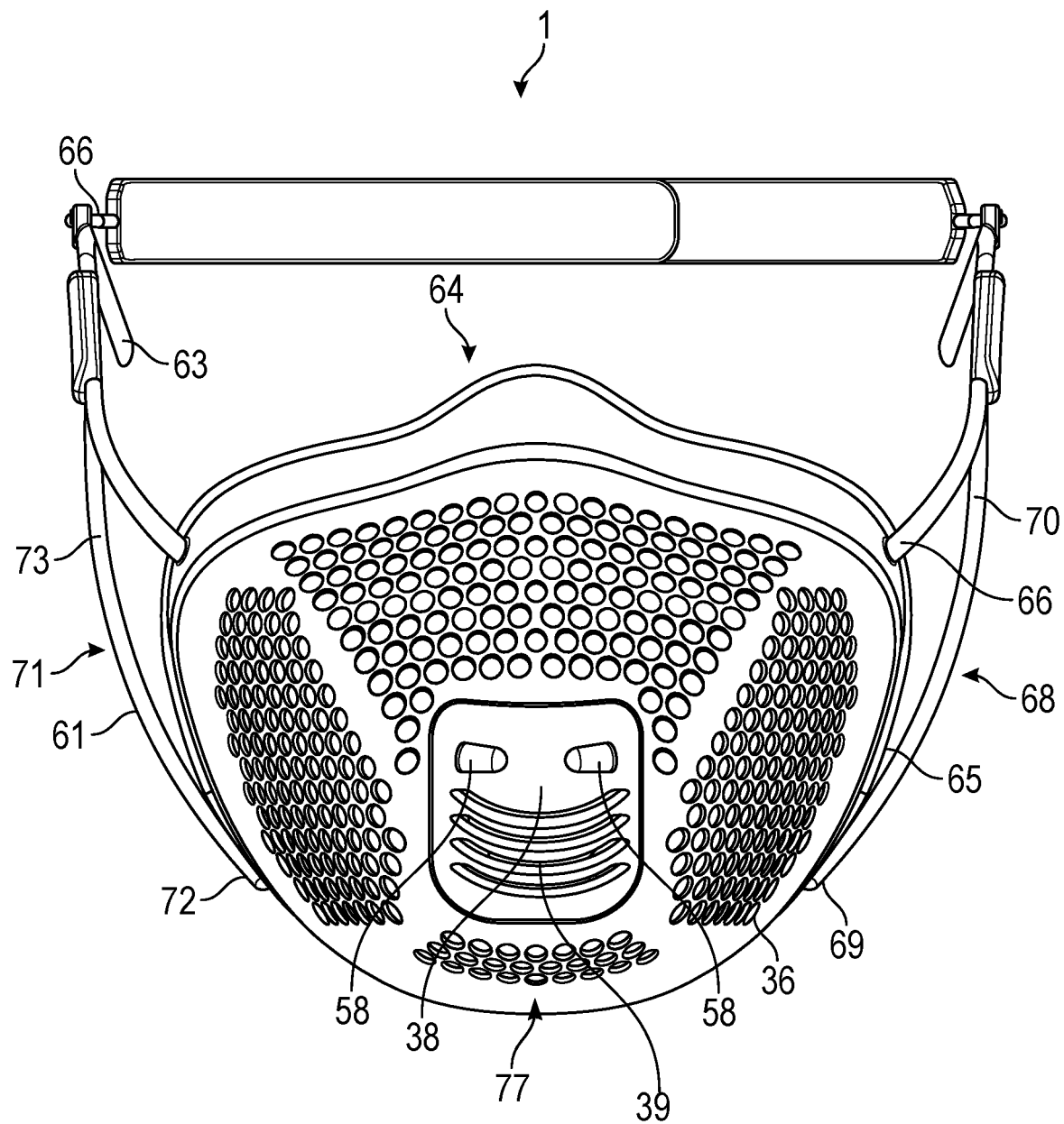
FIG. 3 is a front view of the embodiment of the protection device illustrated in FIG. 1.
Figure 4:
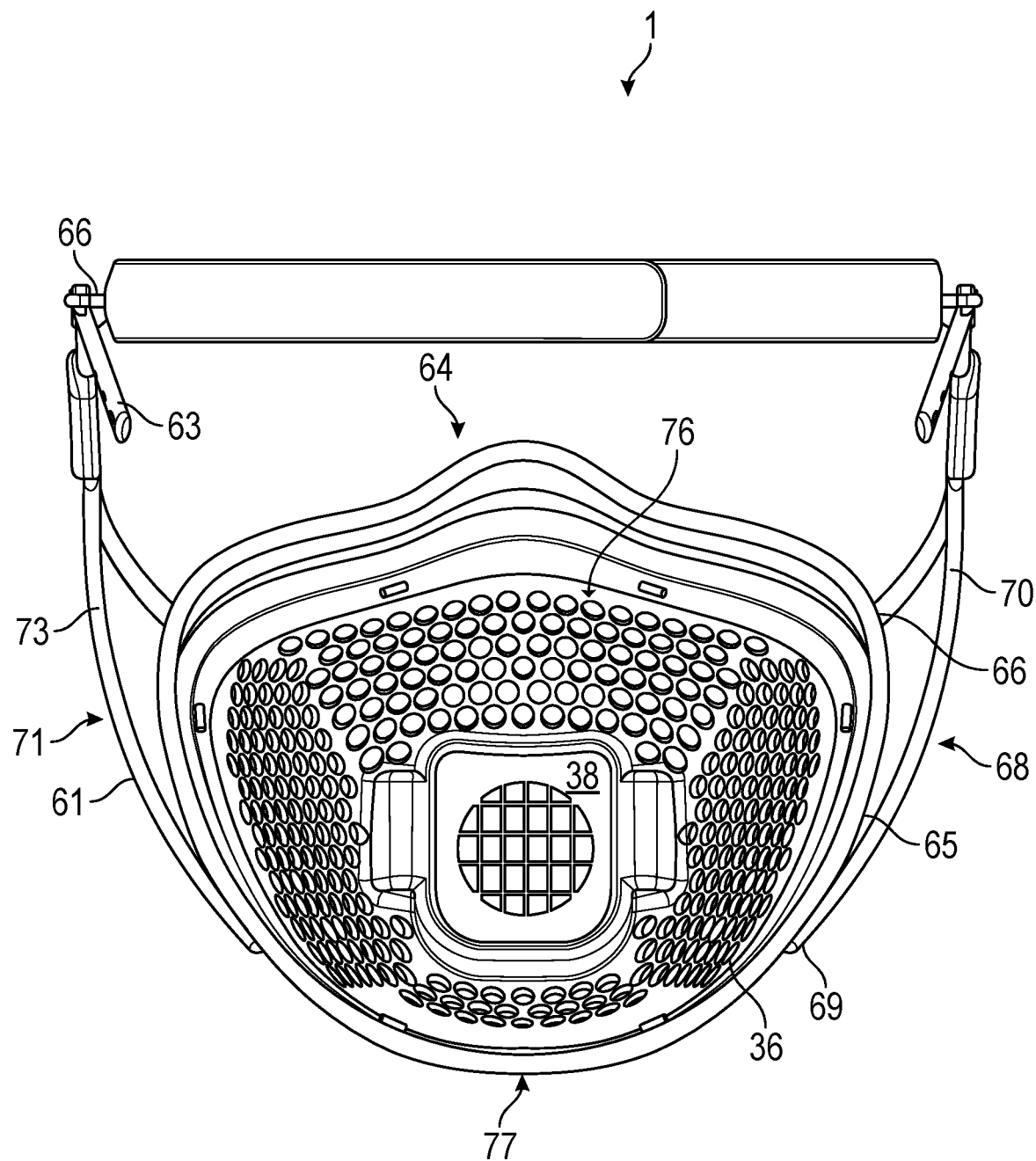
FIG. 4 is a back view of the embodiment of the protection device illustrated in FIG. 1.
Figure 5:
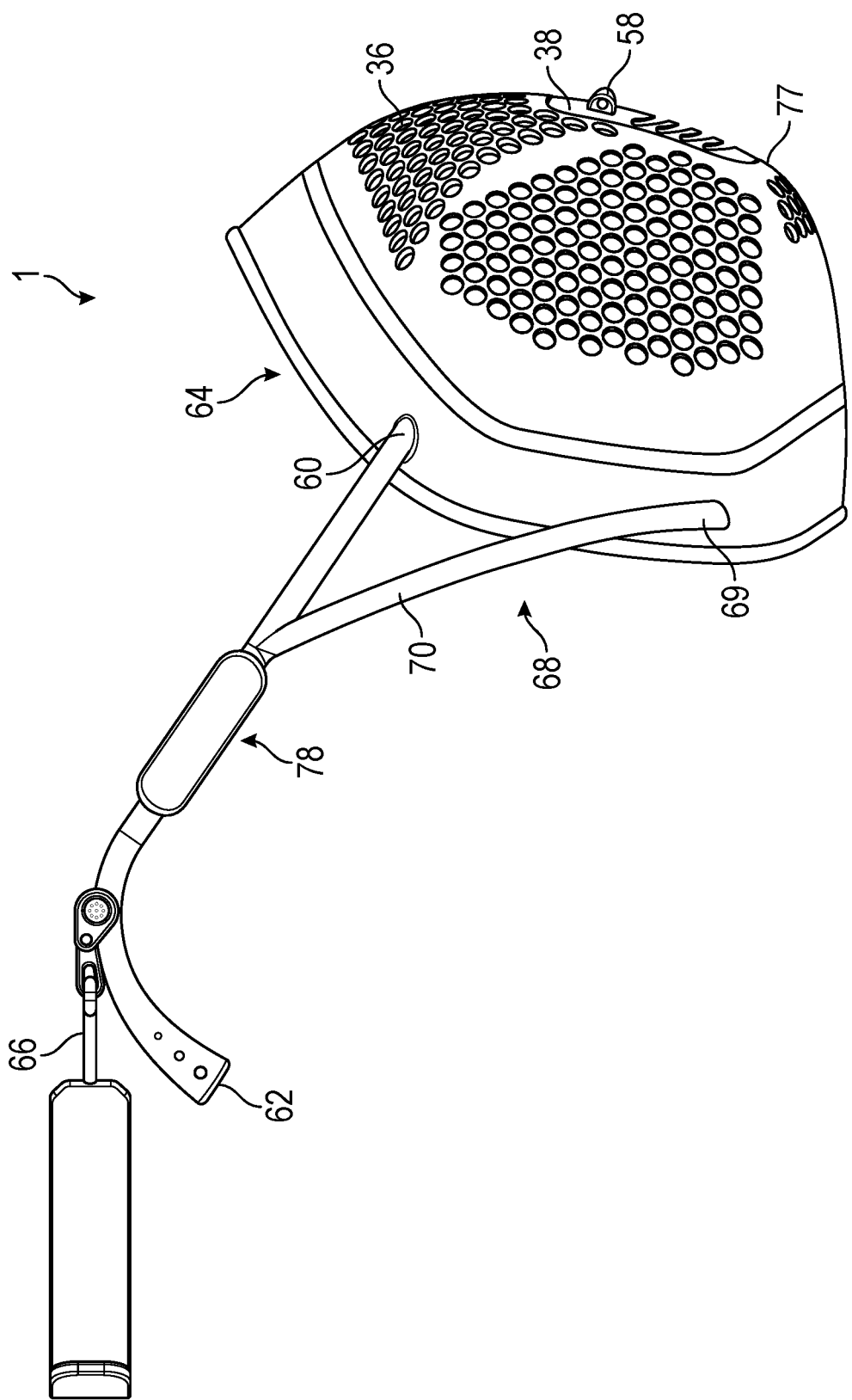
FIG. 5 is a right-side view of the embodiment of the protection device illustrated in FIG. 1.
Figure 6:
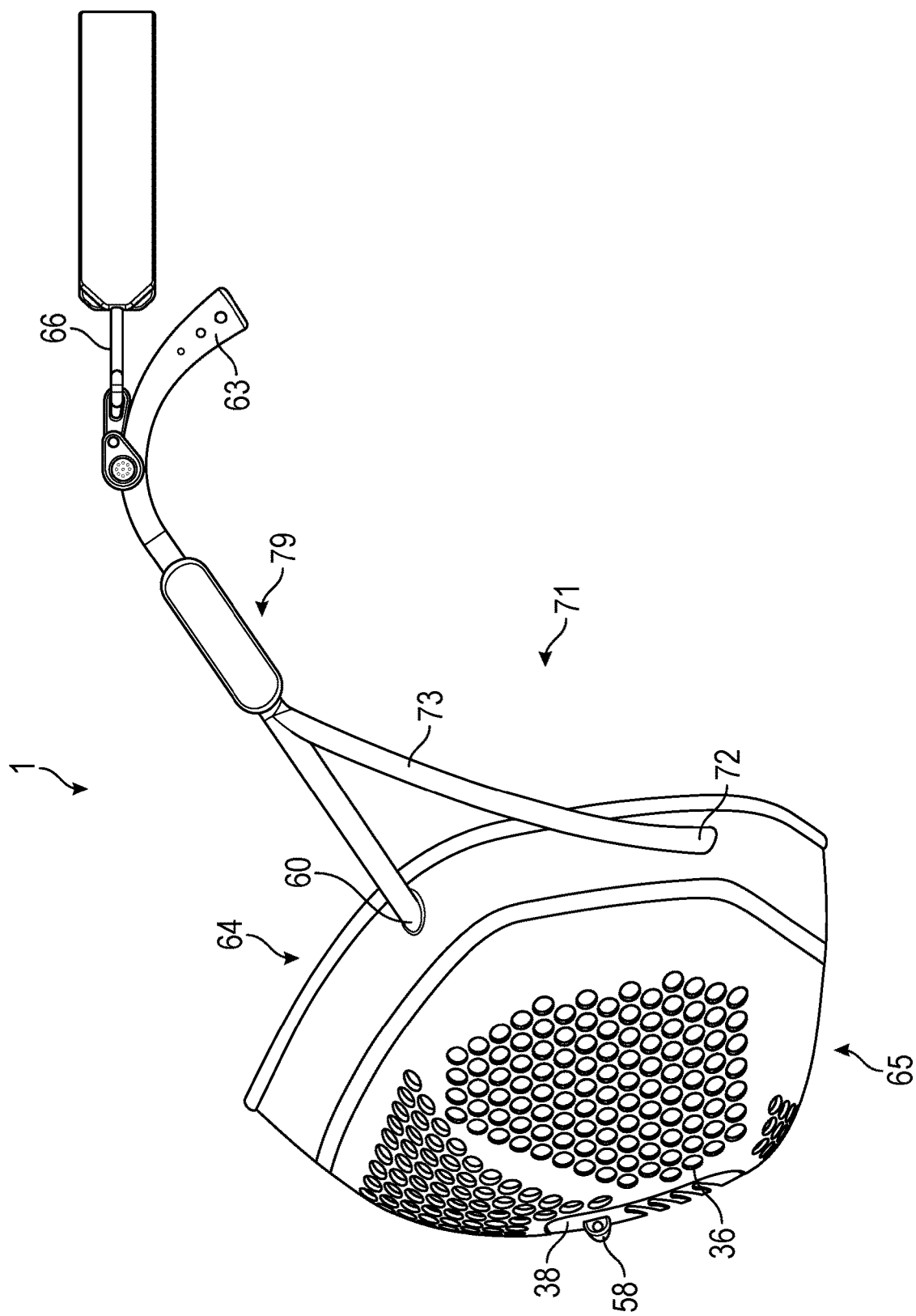
FIG. 6 is a left-side view of the embodiment of the protection device illustrated in FIG. 1.
Figure 7:
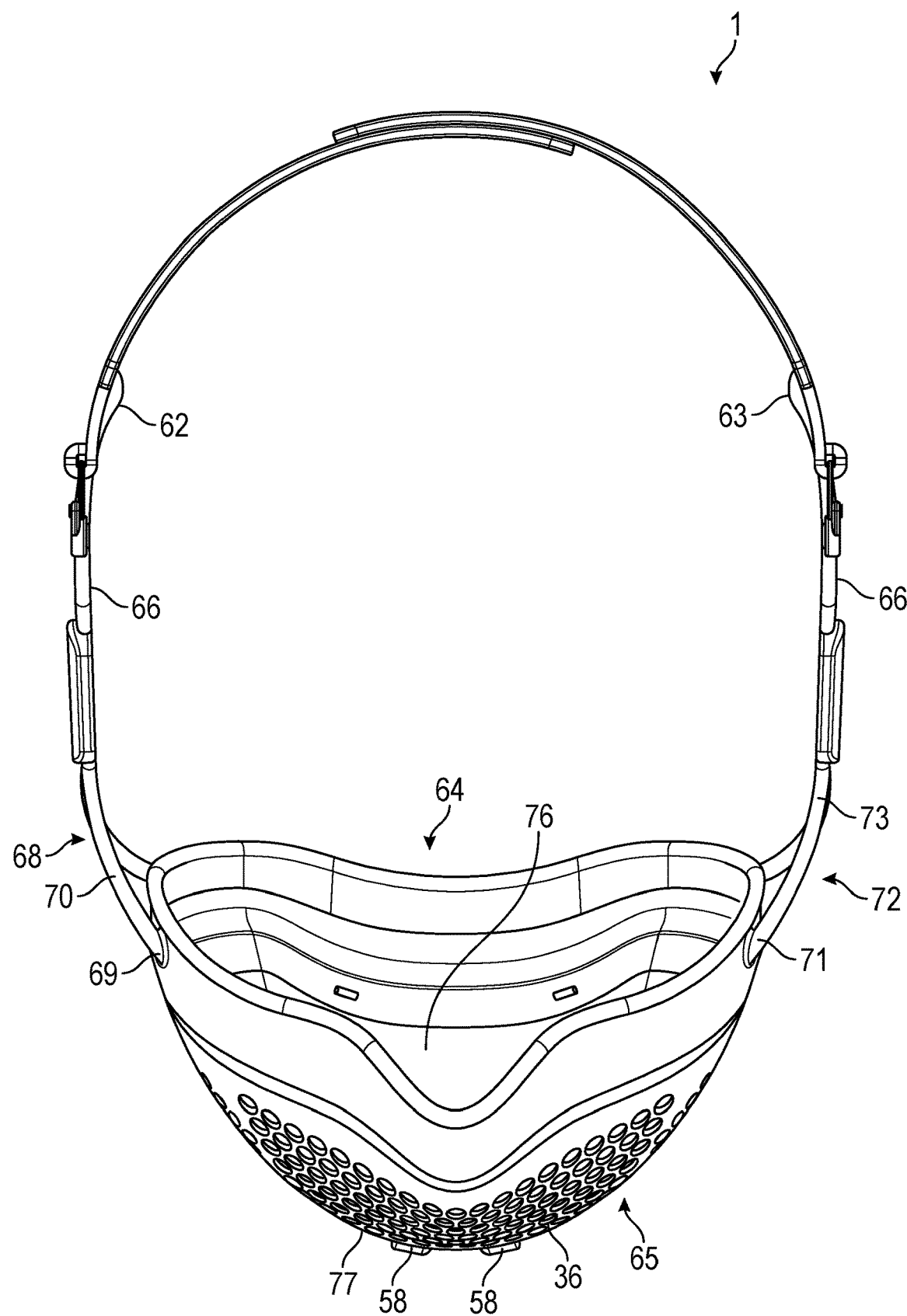
FIG. 7 is a top view of the embodiment of the protection device illustrated in FIG. 1.
Figure 8:
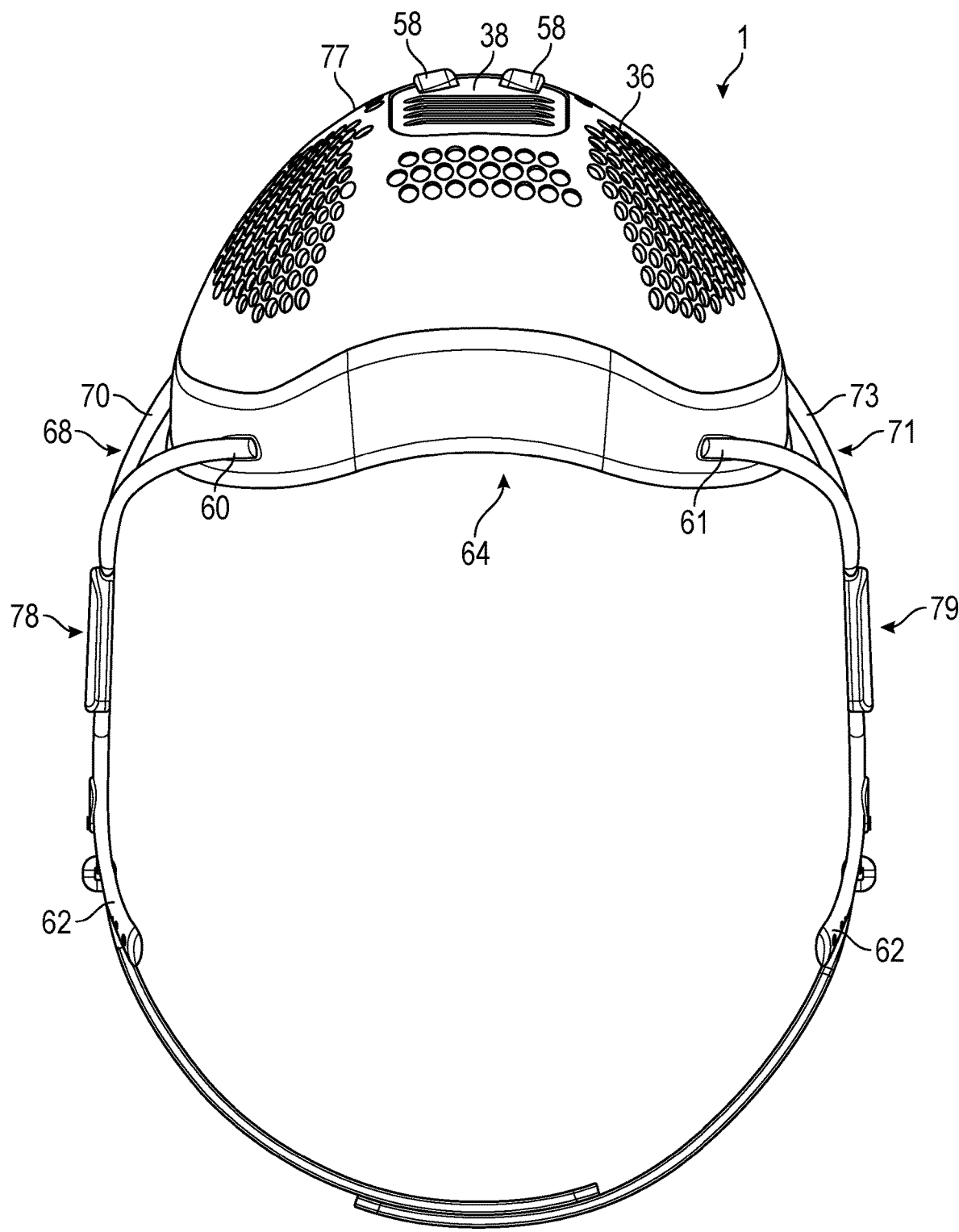
FIG. 8 is a bottom view of the embodiment of the protection device illustrated in FIG. 1.
Figure 9:
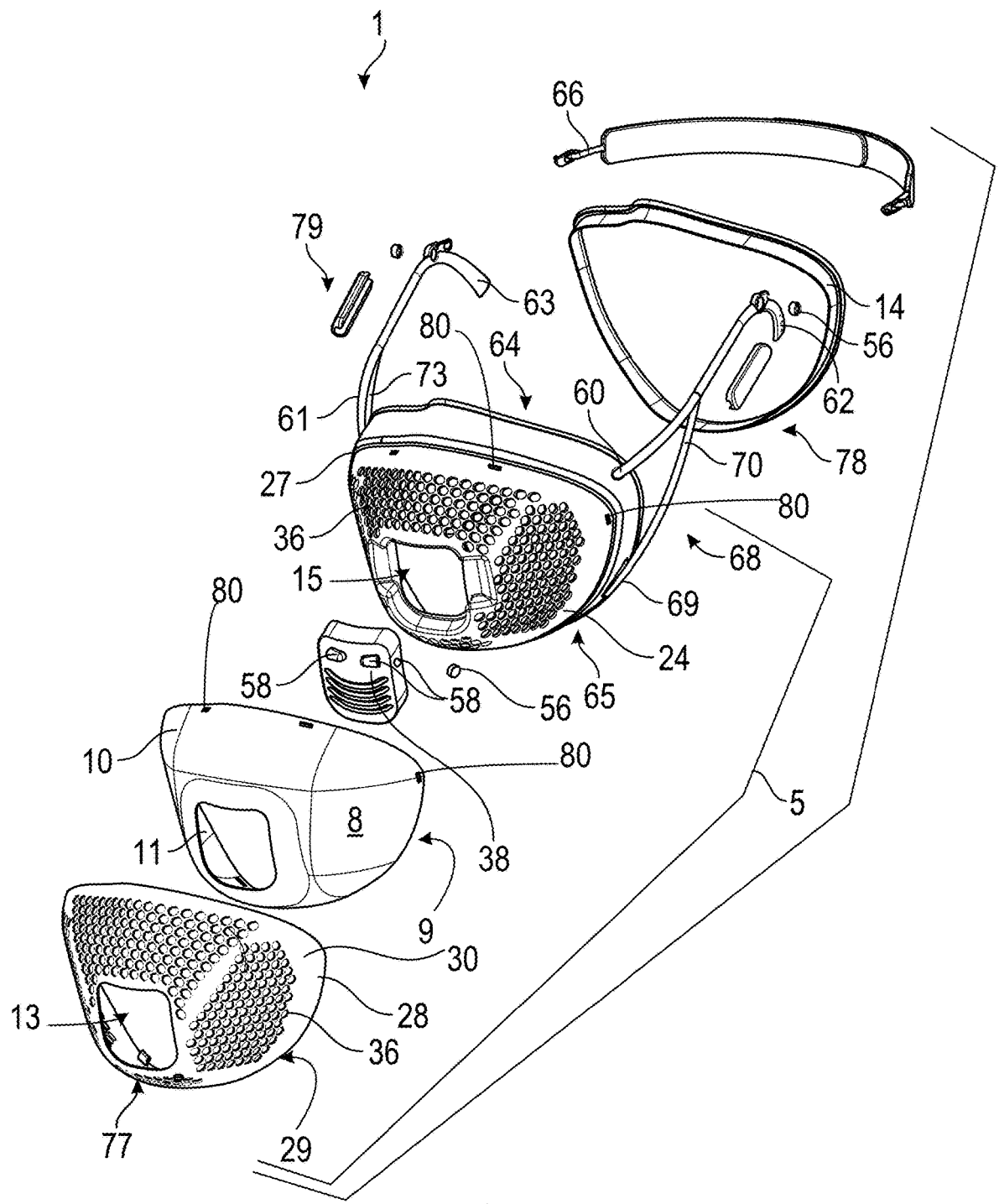
FIG. 9 is an exploded view of an example of the embodiment of the protection device illustrated in FIG. 1.

Several illustrative embodiments of protection devices are described herein. The following is a list of certain components that are described and enumerated in this disclosure in reference to the above-listed figures. Other components, or aspects of these components, may not be included in the list but are disclosed in the figures and description. Accordingly, any aspect illustrated in the figures, whether or not called out separately herein, can form a portion of various embodiments and may provide basis for claim limitation relating to such aspects, with or without additional description. The enumerated components include:

1 protection device
2 protection device
3 protection device
5 filter assembly
8 filter
9 filter proximal surface
10 filter distal surface
11 filter opening
12 frame assembly (frame)
13 distal layer opening
14 seal
15 proximal layer opening
16 first safety compartment (first compartment)
18 second safety compartment (second compartment)
20 seal of first safety compartment seal (first seal)
22 seal of second safety compartment (second seal)
24 filter assembly proximal layer (proximal layer)
26 inner surface proximal layer
27 outer surface proximal layer
28 filter assembly distal layer (distal layer)
29 inner surface distal layer
30 outer surface distal layer
35 second volume
36 aperture (opening)
38 valve
39 vents
40 skirt
42 eye shield
44 left temple arm
46 right temple arm
48 left ear support
50 right ear support
52 electronics module
54 speaker
56 microphone
58 UV-C Light emitting diode (LED)
60 proximal end left temple arm
61 proximal end right temple arm
62 distal end left temple arm
63 distal end right temple arm
64 upper portion
65 lower portion
66 strap
68 left temple arm brace (left brace)
69 left temple arm brace lower end (lower end)
70 left temple arm brace upper end (upper end)
71 right temple arm brace (right brace)
72 right temple arm brace (lower end)
73 right temple arm brace (upper end)
74 skirt lower portion
75 skirt upper portion
76 protection device proximal surface (proximal surface)
77 protection device distal surface (distal surface)
78 left side
79 right side
80 fastener
81 skirt left portion
82 skirt right portion
200 device
201 arm assembly
202 temple arm
204 brace
206 ear support
208 first fastener
210 second fastener
212 earpiece
213 distal end brace
220 proximal end
222 distal end temple arm FIG. 1 is a front perspective view of an example of a first embodiment of a protection device 1 having a filter assembly 5 that is structured to cover a user's nose and mouth and to form a sealed first compartment 16, described below, that encloses the user's nose and mouth to protect inhalation and ingestion of undesired material. Device 1 is described in reference to FIGS. 1-8 and 25 which illustrate the example of the first embodiment, where FIG. 2 is a back perspective view, FIG. 3 is a front view, FIG. 4 is a back view, FIG. 5 is a right-side view FIG. 6 is a left-side view, FIG. 7 is a top view and FIG. 8 is a bottom view. FIG. 9 is an exploded view of this example of a first embodiment and illustrates certain features and characteristics that may not be able to be seen in FIGS. 1-9. Note, for clarity of the illustrations, all of the corresponding depictions of certain features in each of FIGS. 1-9 may not be enumerated even though they illustrate different views of the same feature.

Referring to FIGS. 1-9, device 1 includes a proximal surface 76 that is positioned closest to a user's face with the device is worn, and a distal surface that faces away from a user when the device 1 is worn by the user. Protection device 1 includes a left side 78 and a right side 79. The device 1 includes a filter assembly 5 having a proximal side positionable near a user's face and a distal side positioned away from the user's face. The filter assembly 5 includes a removable (replaceable) filter 8 (FIG. 9), a proximal layer 24 and a distal layer 28. The filter assembly 5 is structured to hold the filter 8 sandwiched between the proximal layer 24 and the distal layer 28. In some embodiments, the proximal and distal layers 24, 28 are translucent. In some embodiments, the proximal and distal layers 24, 28 are transparent, or clear. In some embodiments, the proximal and distal layers 24, 28 are colored (e.g., blue, yellow, orange, green, etc.). The proximal layer 24 includes an inner surface 26 (facing the user when the device 1 is worn) and an outer surface 27 (facing away from the user when the device is worn). The inner surface 26 of the proximal layer 24 forms a portion of the proximal surface 76 or the protection device 1. The distal layer 28 includes an inner surface 29 and an outer surface 30. The outer surface 30 forms a portion of the distal surface 77 of the protection device 1. The proximal layer 24 and the distal layer 28 may comprise a rigid or semi-rigid material. The proximal layer 24 and the distal layer 28 may have corresponding shapes such that they fit closely together with the filter 8 positioned therebetween.

Both the proximal and distal layers 24, 28 have a plurality of openings 36 that allow air to pass through these layers 24, 28 while they provide supporting surfaces to hold the filter 8 and protect the integrity of the filter 8, preventing objects larger than the openings 36 from contacting the filter 8. The openings 36 can be circular (as shown in this example), or have a different shape (e.g., oval, rectangular, star-shaped, etc.). The openings 36 can be arranged in a variety of patterns. The total area of the openings 36 is sufficiently large to support breathing by the user. In some embodiments, some or all of the openings on the proximal layer 24 and the distal layer 28 are aligned to ensure air flow through the filter assembly 5 is unimpeded, except for the filter 8.

The filter 8 includes a proximal surface 9 and a distal surface 10 positioned opposite the proximal surface 9. In some embodiments, the filter 8 is translucent. In some embodiments, the filter 8 is transparent, or clear. In some embodiments, the filter is a transparent and colored (e.g., blue, yellow, orange, green, etc.). The filter 8 is configured to prevent airborne material from passing through the filter. In some embodiments, the filter is configured to prevent 90% of airborne solid particles from passing through the filter. In some embodiments, the filter is configured to prevent about 91%, 92%, 93%, 94%, 95%, 96%, 97%, 98%, 99%, or more than 99% (+/−05%), of airborne solid particles from passing through the filter. In some embodiments, the filter 8 is classified as an N95 filter. In some embodiments, the filter is classified as a N99 filter.

The filter 8 may be designed and structured to filter certain types of material, and the filter 8 can be changed based on its use condition. For example, when used in a medical environment under "normal" user exertion conditions, the filter 8 can be designed and constructed to filter viruses and other microscopic material. Such filters may restrict airflow more so than other designs but with the benefit of providing a higher degree of filtering. A filter 8 for use in a construction environment, under moderate or heavy exertion conditions may be designed and constructed to filter out larger materials but allow a less restrictive airflow. Thus, the removable/replaceable filter provides an advantage of being able to select a filter based on the use conditions.

The filter 8 includes an opening 11 which is shaped and sized to fit closely around a one-way valve 38. In this example, the opening 11 is rectangular shaped. However, the opening 11 can be any shape or size that corresponds with the valve 38. The distal layer 28 also includes an opening 13 shaped and sized to fit around the valve 38. The proximal layer 24 also includes an opening 15, the valve 38 being positioned in the opening 15 and coupled to the proximal layer 15. The valve 38 allows for air exhaled from a user to flow through the valve from the proximal side of the filter assembly 5 to the distal side, and prevents air from flowing through the valve from the distal side of the filter assembly 5 to the proximal side. In this example, a single valve 38 is positioned in a center portion of the filter assembly. Other embodiments may include one or more valves positioned on other portions of the filter assembly 5, for example, on one or both sides of the center of the filter assembly 5. The valve 38 can have various configurations. Various designs of valves can be employed. In this example, the valve includes one or more vents 39 that direct an air flow, passing through the valve, in a downward direction. In some embodiments, the valve 38 is translucent or transparent.

In some embodiments, the device 1 includes a microphone 56 coupled to the valve 38. The microphone 56 can be a wireless or wired microphone, and can be part of a communication circuit that is integrated into the device 1. In some embodiments, one or more UV-C LED's 58 can be coupled to the valve 38. The example in FIG. 1 includes two LED's 58a positioned on the distal side of the valve 58. The LED's 58 are aligned to emit UV-C radiation onto a portion of the outer surface 30 of the distal layer 28 to sanitize air prior to the air passing into and through the filter assembly 5. This example also includes two UV-C LED's 58 positioned on a side portion of the valve 38 as shown in FIG. 9, one UV-C LED 58 aligned to emit radiation towards a left side 78 of the device 1 and the other UV-C LED 58 aligned to emit radiation towards a right side 79 of the device 1. When air is inhaled through the filter assembly 5, material including pathogens can accumulate on the distal side of the filter 8. The UV-C LED's 58 positioned on a side portion of the valve 38 are aligned to emit UV-C radiation onto and along the filter distal surface 10 to neutralize/kill viruses that accumulate on the distal surface 10 of the filter 8.

The device 1 also includes a seal 14 positioned along a continuous peripheral edge of the filter assembly 5. The filter assembly 5 and the seal 14 define a first safety compartment 16 (FIG. 2) having a first volume 33. The first compartment 16 is structured to surround and enclose a user's mouth and nose within the first volume 33. In the examples of the first embodiments (e.g., FIGS. 1-9) and the second embodiment (e.g., FIGS. 10-18) the seal 14 can be referred to as a first safety compartment seal 20 for the first safety compartment 16. In the example of the third embodiment (e.g., FIGS. 19-27), the seal 14 can be referred to as being a first seal 20 for the first safety compartment 16 and a second seal 22 for the second safety compartment, the second seal 22 positioned along the peripheral edge of the second safety compartment 18 forming a tight seal with a portion of the user's face. The second safety compartment 18 is structured to surround and enclose a user's eyes within a second volume 35, the second seal 22 defining the outer edge of the second safety compartment 18.

The device 1 also includes a frame assembly ("frame") 12 coupled to the filter assembly 5 for attaching the device 1 to the head of a user. The frame 12 includes a left temple arm 44 having a proximal end 60 coupled to an upper portion 64 of the filter assembly 5, and a right temple arm 46 having a proximal end 61 coupled to the upper portion 64 of the filter assembly 5. In this example, the frame 12 also includes a left temple arm brace 68 coupled to the left temple arm 44 at an upper end 70. The left brace 68 extends towards a lower portion 65 of the filter assembly 5. The lower end 69 of the left brace 68 is coupled to the lower portion 65 of the filter assembly 5. The frame 12 also includes a right temple arm brace 71 coupled to the right temple arm 46 at an upper end 73. The right brace 71 extends towards a lower portion 65 of the filter assembly 5. The lower end 72 of the right brace 71 is coupled to the lower portion 65 of the filter assembly 5. The frame 12 can be formed from a rigid or semi-rigid material (e.g., plastic, a polymer, rubber, silicon, etc.). The frame 12, or portions of the frame 12, can be translucent or transparent. The frame 12 also includes a left ear support 48 and a right ear support 50. A portion of the ear supports 48, 50 are configured to be placed on a user's ears, and the ear supports 48, 50 can extend behind a user's ears. In some embodiments including this example, a portion of the ear supports 48, 50 are configured to curve behind a user's ears.

In some examples, a communication circuit 52 can be incorporated into the device 1. In FIG. 1 and other figures, a communication circuit 52 is shown as a visible structure on or attached to a temple arm, as one example of it's placement on the device. In other embodiments, the communication circuit 52 is not visible, or is only partially visible, and is integrated into the structure of the protection device 1. The communication circuit 52 can include wireless or wired communication functionality. For example, the communication circuit 52 can include one or more speakers 54 can be positioned on the temple arms distal ends 62, 63. In some embodiments, the speakers 54 can be housed in the ear supports 48, 50. Speakers, and other portions of a communications circuit, housed within the ear supports 48, 50 can advantageously provide additional weight at a point behind the portion of the ear support that rests on the user's ears, the weight helping to hold the ear support firmly against the user's ear to hold the device 1 in place. The communications circuit 52 can also include the microphone 56. In some embodiments, the communications circuit 52 can include wires that are incorporated into the frame 12 and/or the filter assembly 5 connecting components of the communications circuit. The communication circuit 52 can also include wireless components (e.g., microphone, speakers, transmitter, receiver, etc.). In this example, a portion of the communications circuit 52 is illustrated as being positioned on the left and right temple arms 44, 46. In other examples, all or a portion of the communications circuit 52 is positioned within the frame 12 and/or the filter assembly 5. In some embodiments, the communication circuit 52 is operable to communicate wirelessly (e.g., via Bluetooth), or through a wired connection, to a user computing device, e.g., a smart phone, tablet computer, laptop computer, etc. In other embodiments, the communication circuit is configured to provide cell phone functionality, or other communication functionality itself (e.g., via radio communications).

The device 1 can also include a strap 66 which is structured to hold the device onto a user's head. The strap 66 can attach to the distal end 63 of the right temple arm and the distal end 62 of the left temple arm.

Figure 10:
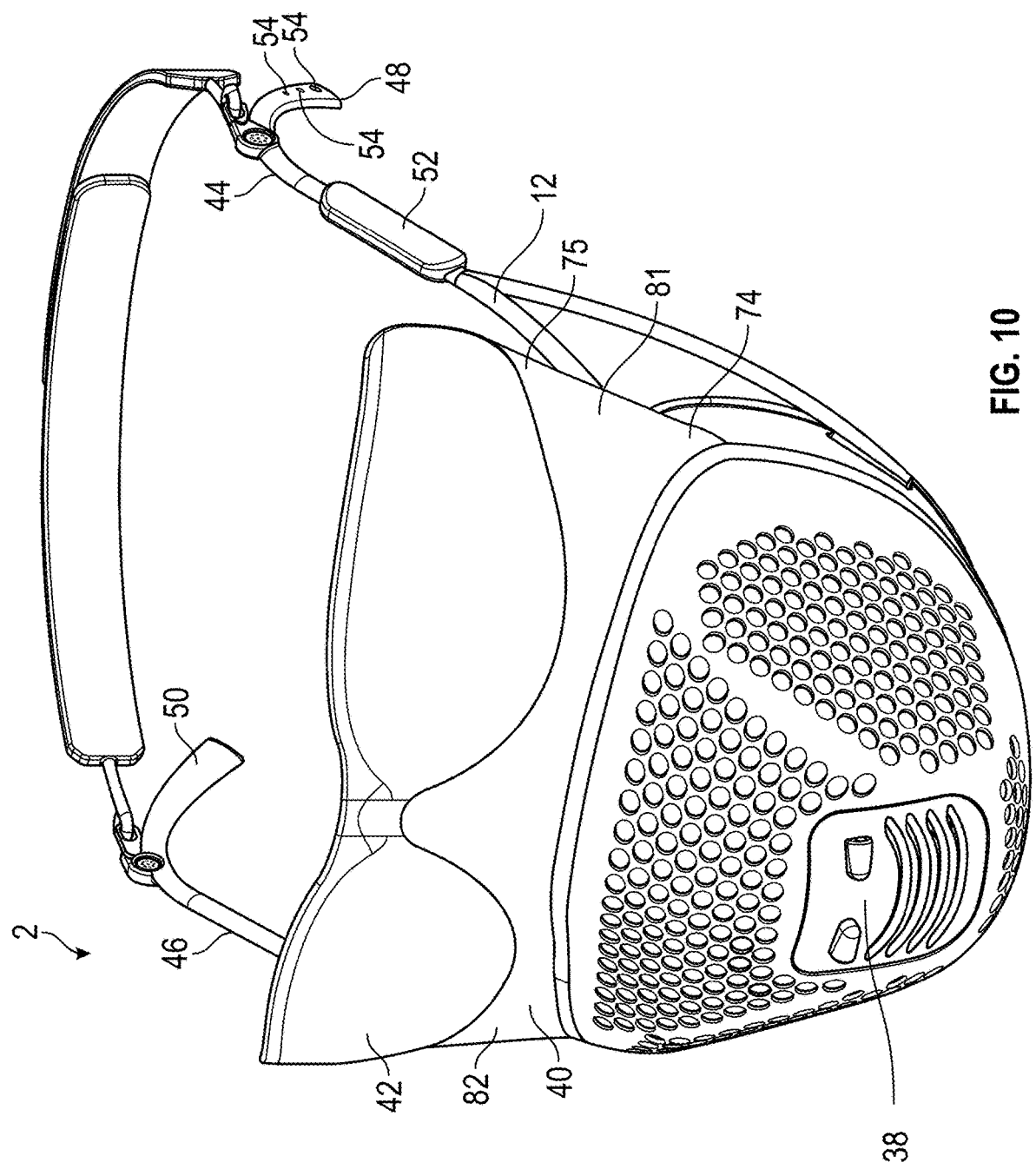
FIG. 10 is a front perspective view of an example of a second embodiment of a protection device having a filter assembly that is structured to cover a user's nose and mouth and to form a sealed compartment that encloses the user's nose and mouth, and having an upper portion that includes a skirt that extends to an eye shield, where in various examples the protective device can also include one or more other features, including for example, a microphone, earpieces, and/or other communication circuits, and UV-C light emitting diodes (LEDs).
Figure 11:
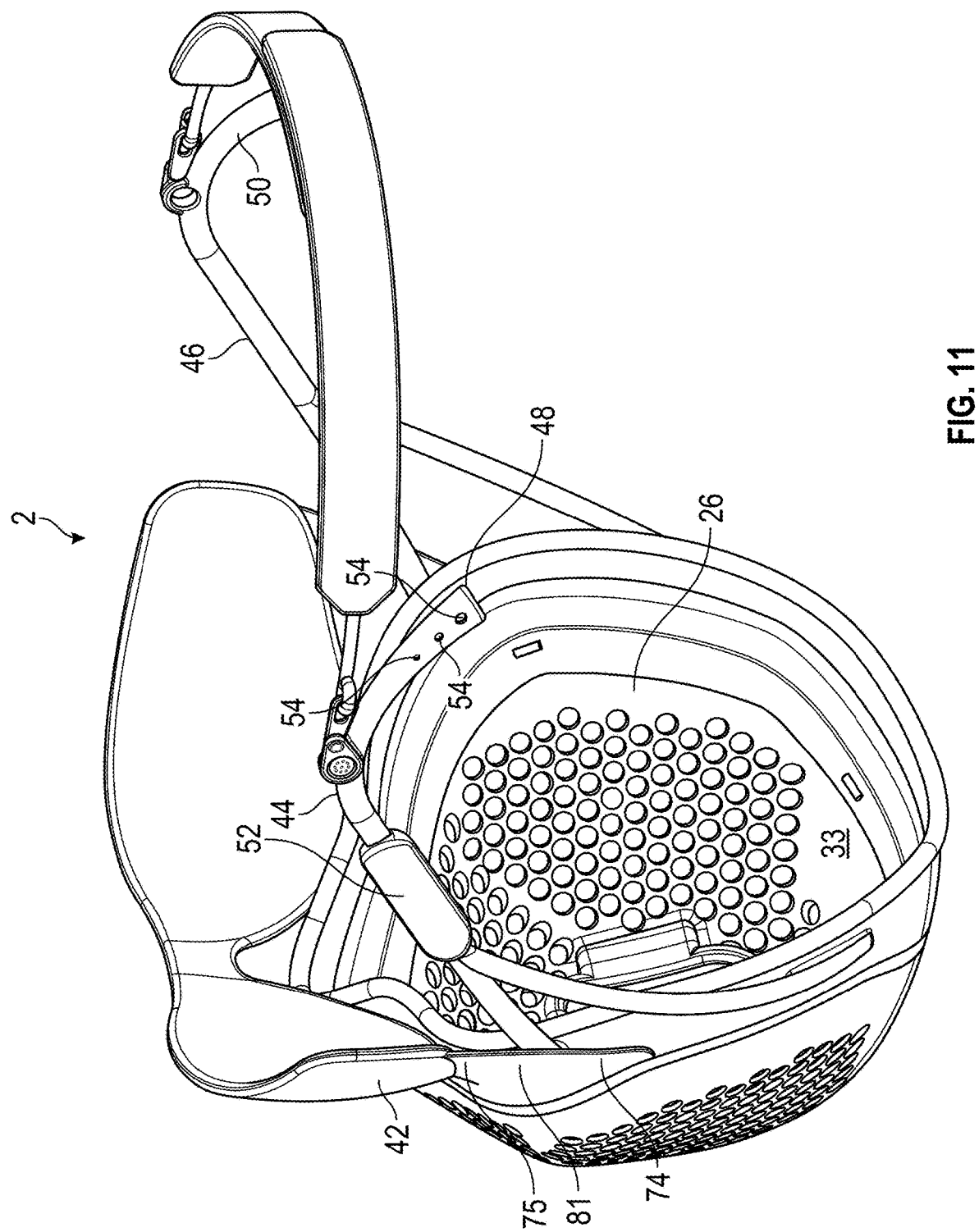
FIG. 11 is a back perspective view of the protection device illustrated in FIG. 10.
Figure 12:
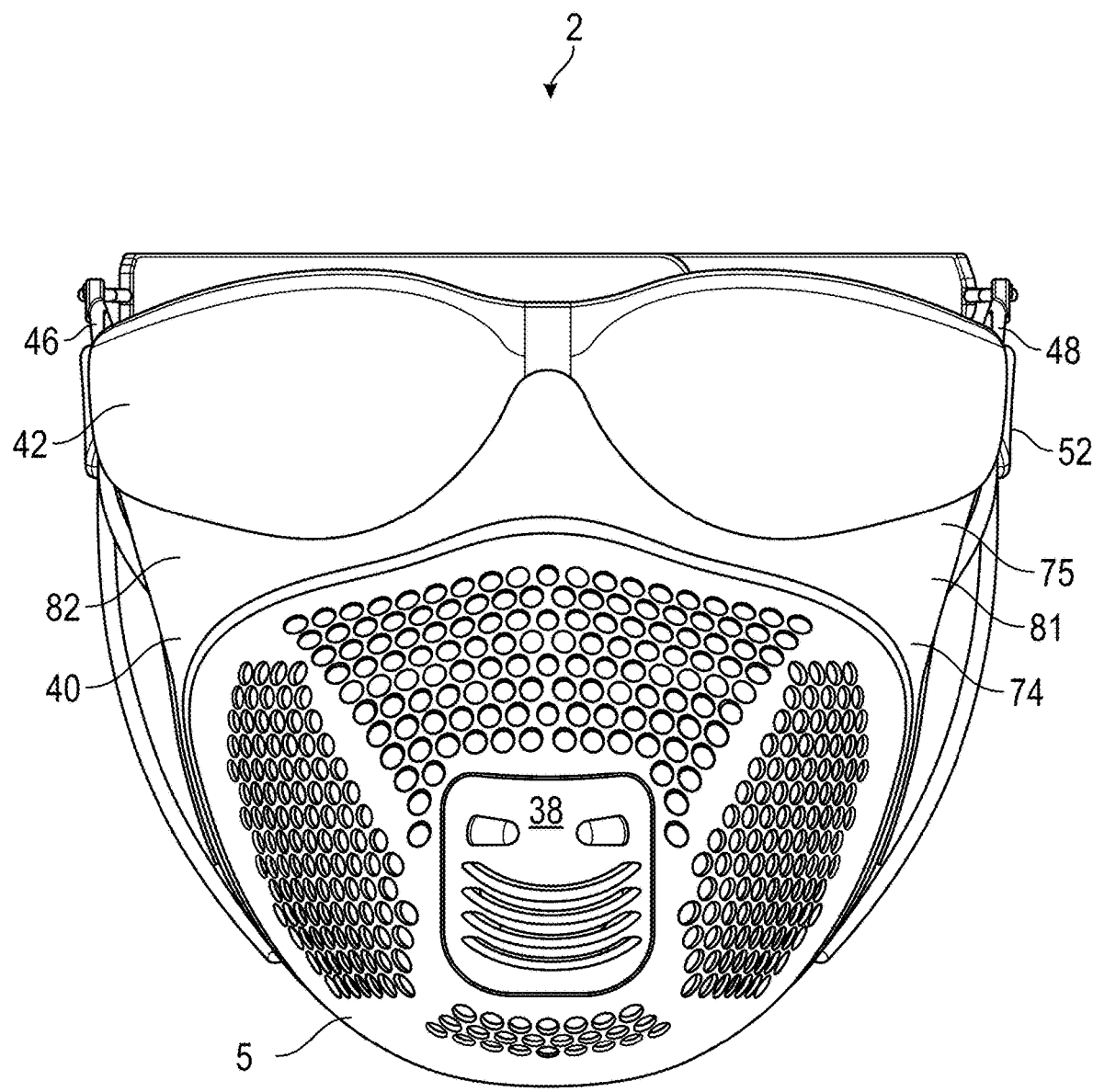
FIG. 12 is a front view of the embodiment of the protection device illustrated in FIG. 10.
Figure 13:
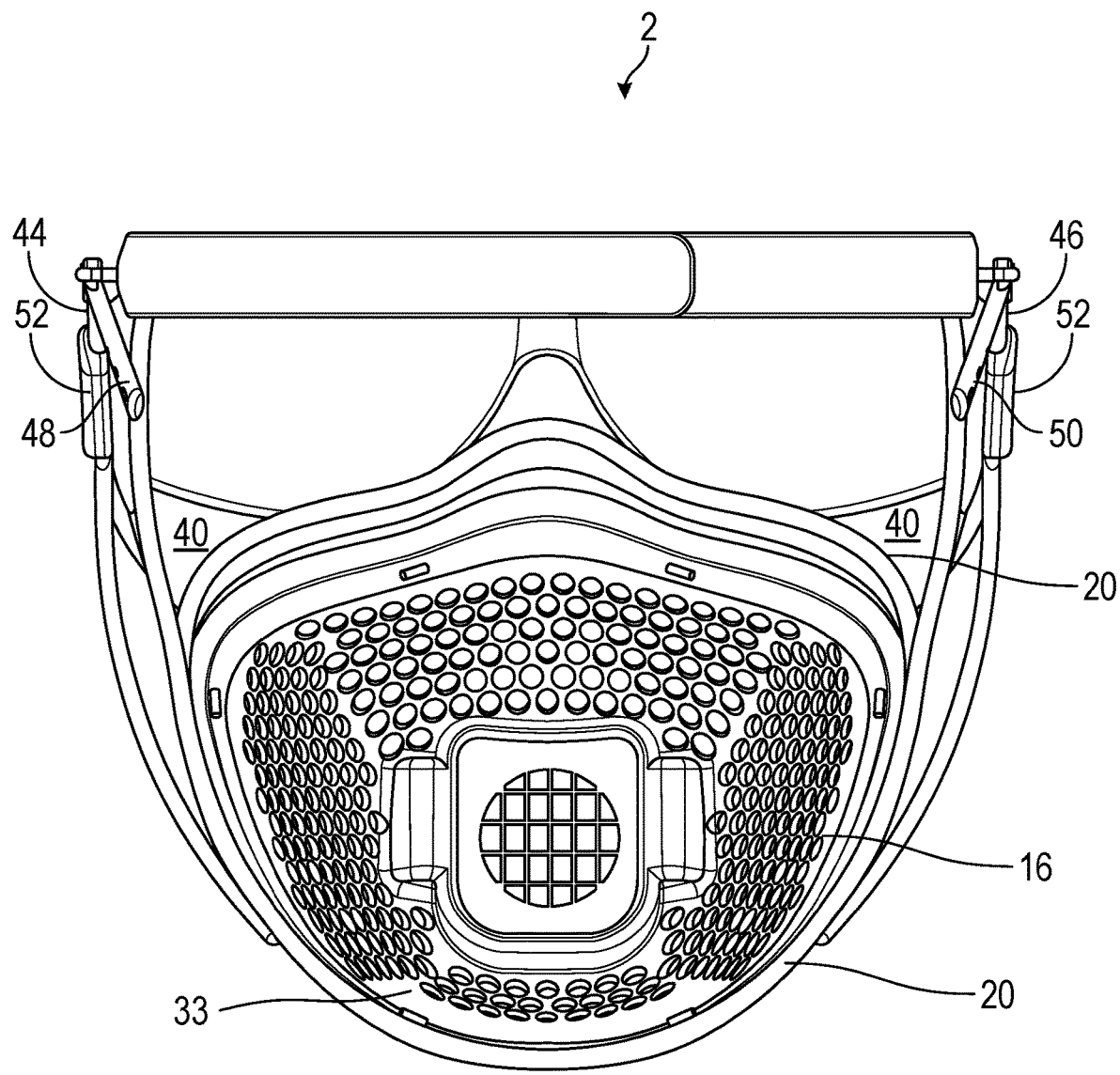
FIG. 13 is a back view of the embodiment of the protection device illustrated in FIG. 10.
Figure 14:
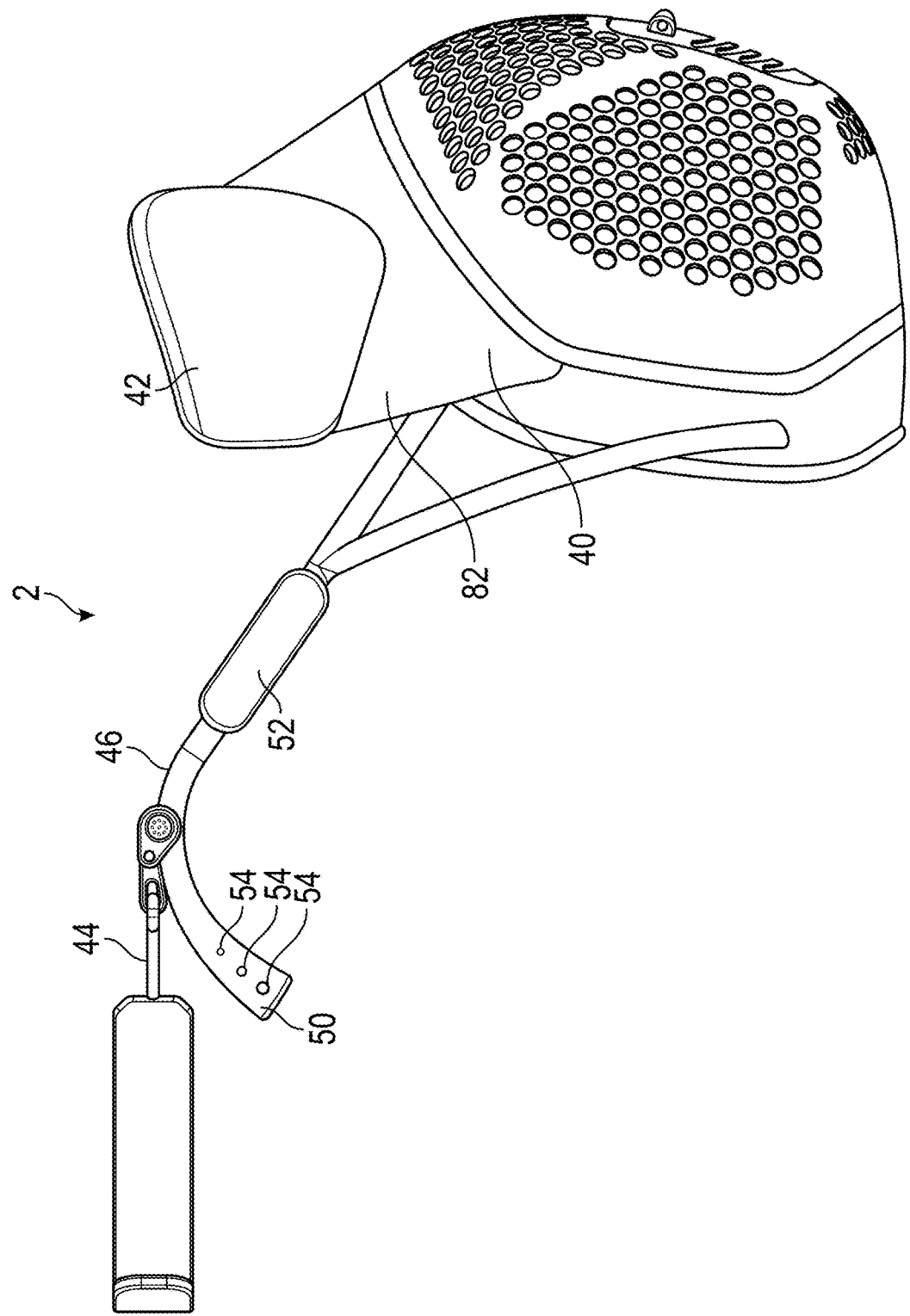
FIG. 14 is a right-side view of the embodiment of the protection device illustrated in FIG. 10.
Figure 15:
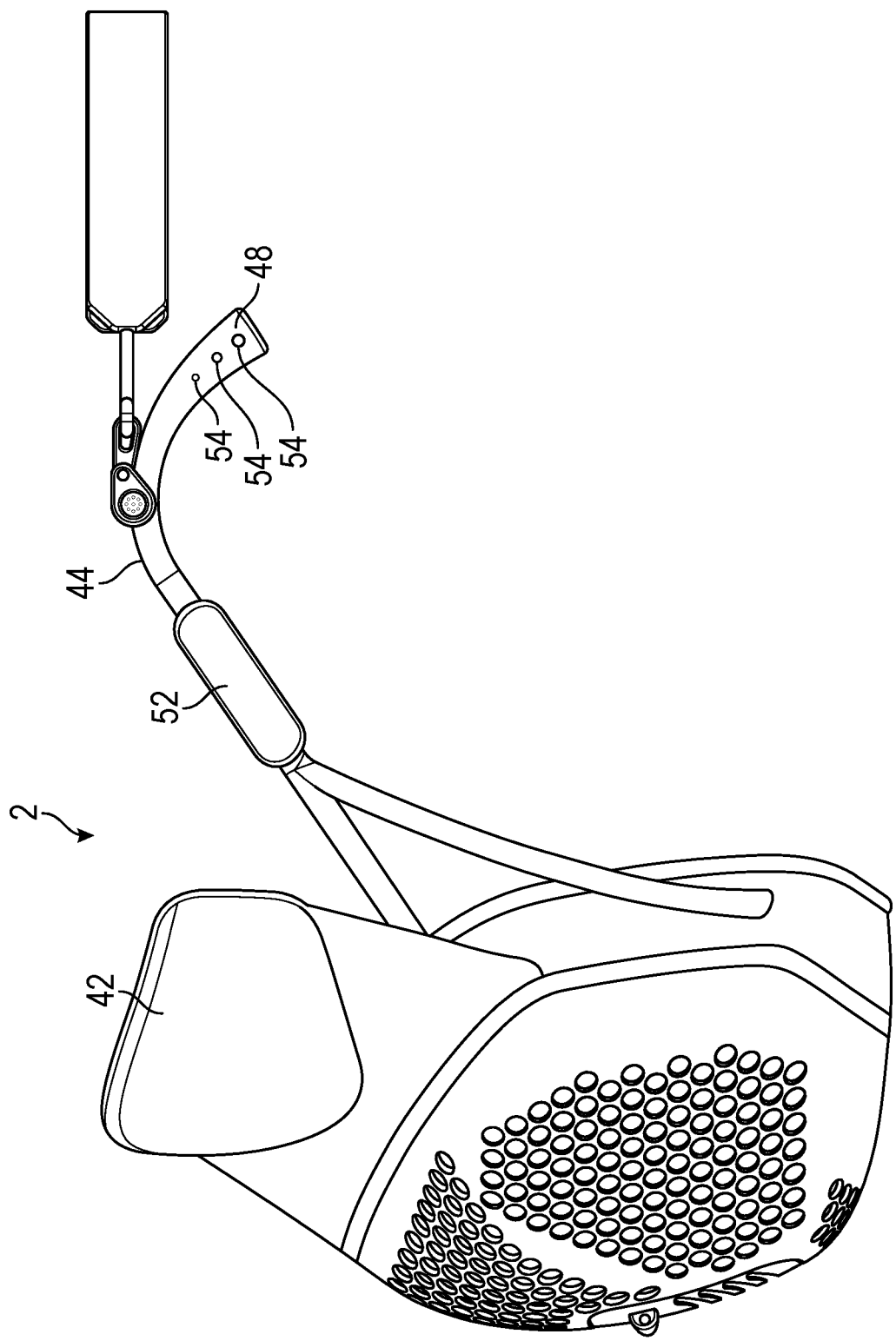
FIG. 15 is a left-side view of the embodiment of the protection device illustrated in FIG. 10.
Figure 16:
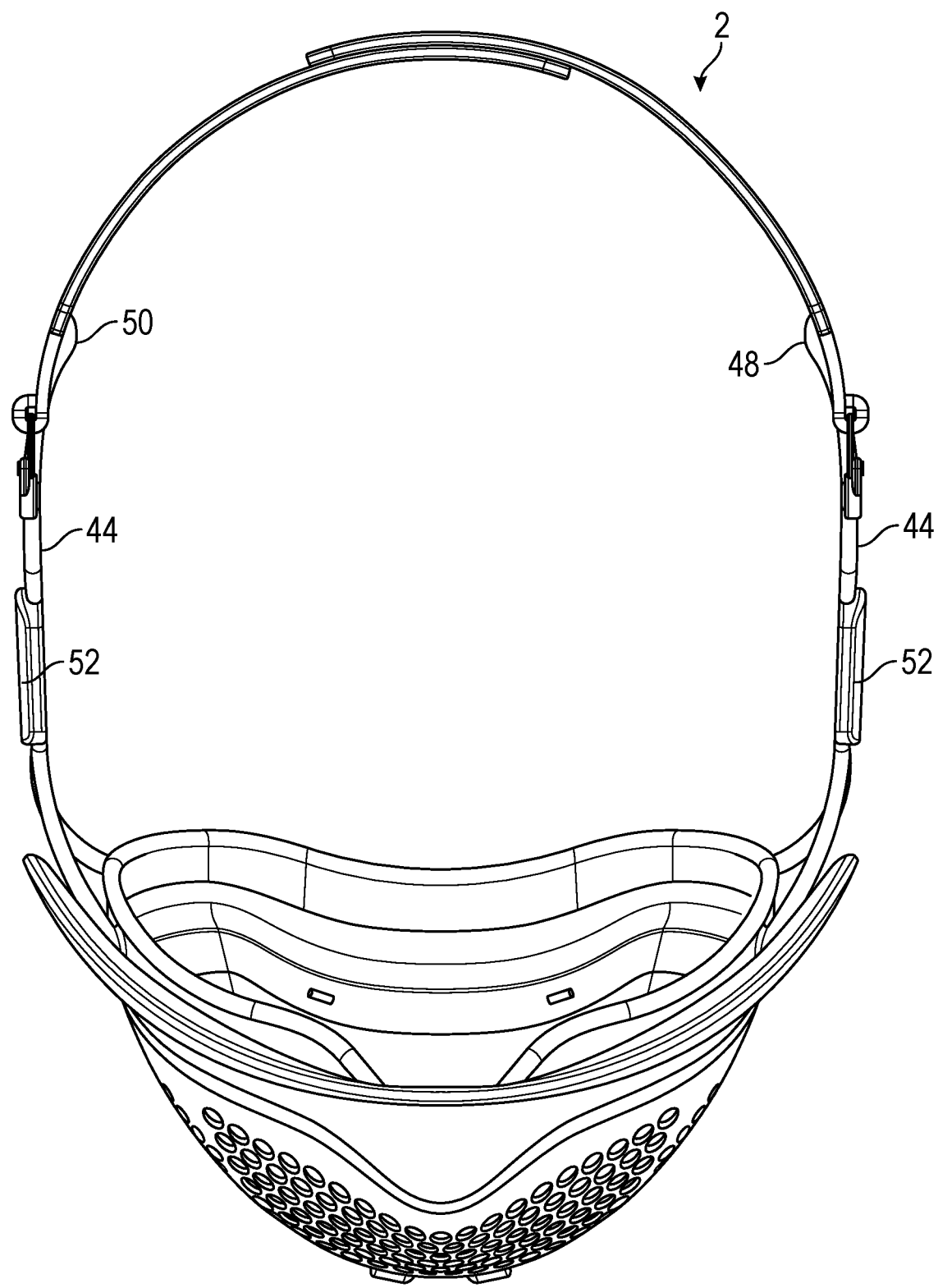
FIG. 16 is a top view of the embodiment of the protection device illustrated in FIG. 10.
Figure 17:
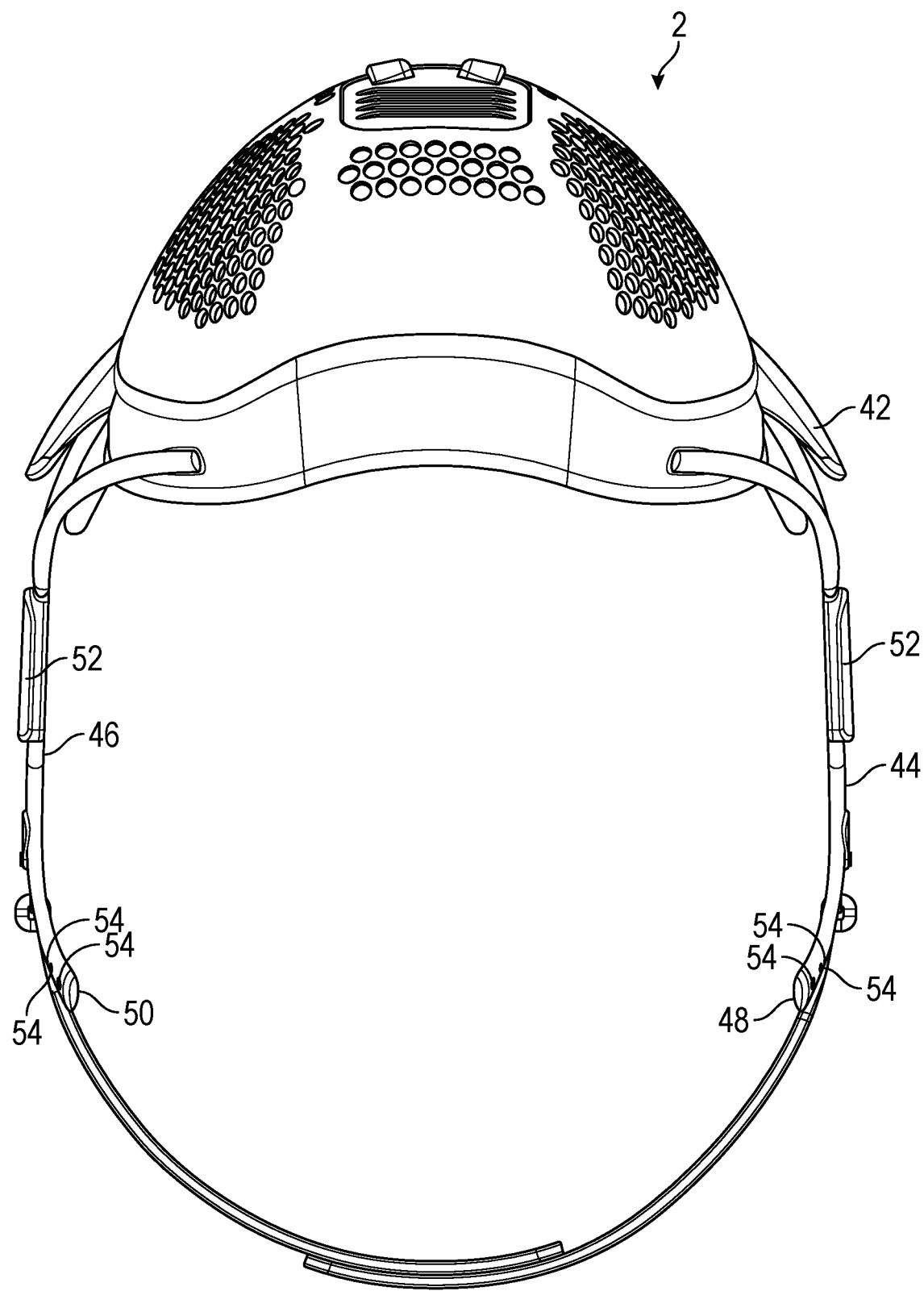
FIG. 17 is a bottom view of the embodiment of the protection device illustrated in FIG. 10.
Figure 18:
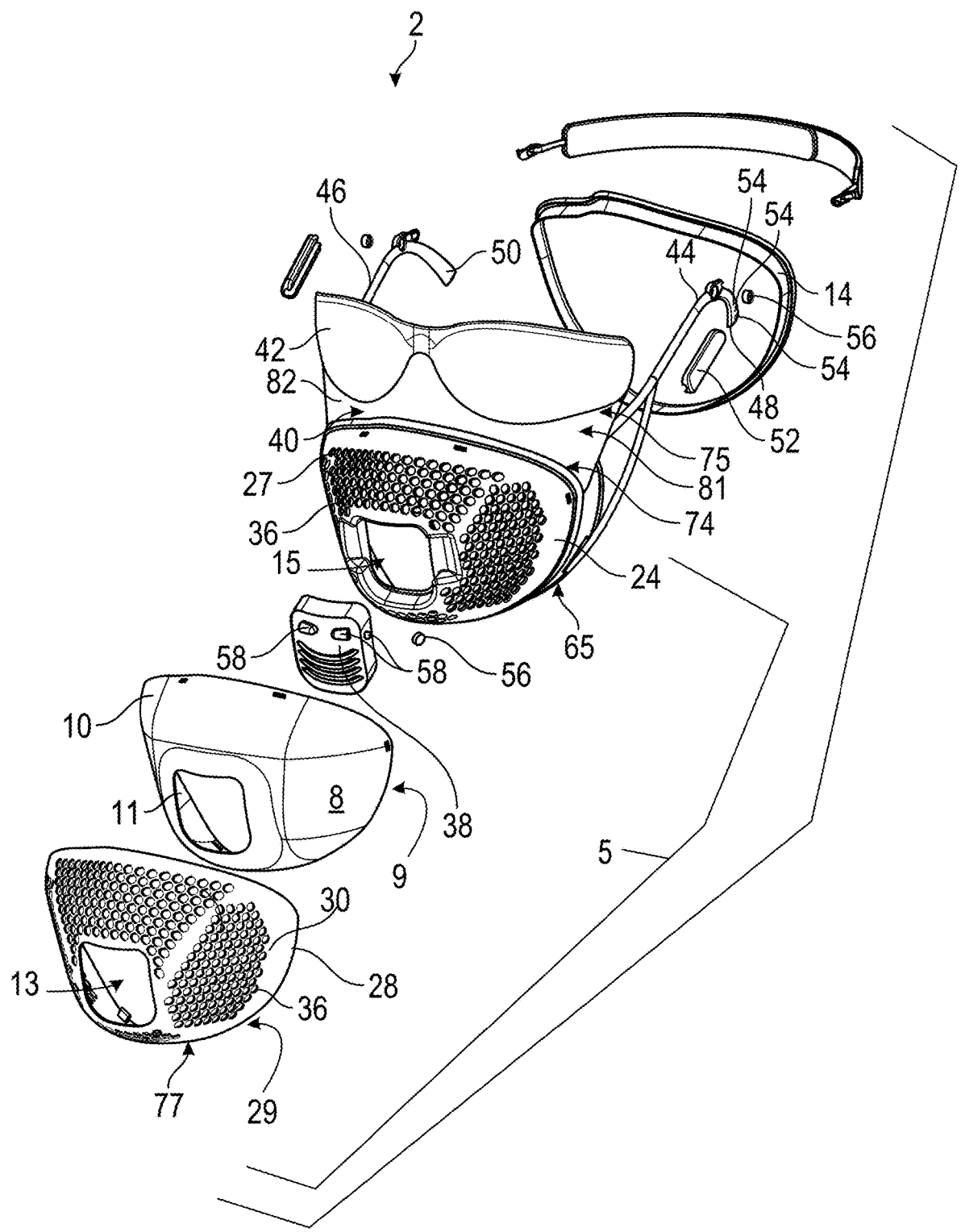
FIG. 18 is an exploded view of an example of the embodiment of the protection device illustrated in FIG. 10.

FIG. 10 is a front perspective view of an example of a second embodiment of a protection device 2 having a filter assembly 5 that is structured to cover a user's nose and mouth to protect inhalation and ingestion of undesired material, and to form a sealed compartment 16 that encloses the user's nose and mouth. Device 2 also has an upper portion that includes a skirt 40 that extends to an eye shield 42. Device 2 is described in reference to FIGS. 10-18 and 26 which illustrate the example of the second embodiment, where FIG. 10 is a front perspective view, FIG. 11 is a back perspective view, FIG. 12 is a front view, FIG. 13 is a back view, FIG. 14 is a right-side view, FIG. 15 is a left-side view, FIG. 16 is a top view, and FIG. 17 is a bottom view. FIG. 18 is an exploded view of this example of the second embodiment and illustrates certain features and characteristics that may not be able to be seen in FIGS. 10-18. Note, for clarity of the illustrations, all of the corresponding depictions of certain features in each of FIGS. 10-18 may not be enumerated even though they illustrate different views of the same feature. Protection device 2 may have many structural features that are the same or similar to features of protection device 1 as illustrated in FIGS. 1-9 and described above in reference to protection device 1. For example, the filter assembly 5, the valve 38, the temple arms 44, 46, left and right brace 68, 71, the ear supports 48, 50, microphone 56, speakers 54, communication circuit 52, strap 66, etc., and the description of any similar features of device 1 applies to device 2 as well. Protection device 2 also has some different structural features that are different as discussed below.

As illustrated in FIGS. 10-18, protection device 2 includes a skirt 40 that extends from the filter assembly 5 to an eye shield 42. In various embodiment, the skirt 40 can be a rigid, semi-rigid or a pliable material. An upper portion of the skirt 40 is coupled to a lower portion of the eye shield 42 along a bottom edge of the eye shield 42 forming a protective barrier that covers the portion of a user's face between their mouth and nose, and their eyes.

Protection device 2 also includes a seal 14 that is positioned along the edge of the filter assembly 5. Similar to protection device 1, the filter assembly 5 and the seal 14 define the first safety compartment 16, partially enclosing a volume that can cover a user's mouth and nose and seal tightly against the user's face, such that any air that enters the user's nose or mouth passes through the filter 8. As shown in FIGS. 10 and 11, the seal 14 is positioned behind the skirt 40, that is, proximal to a user's face relative to the skirt 40.

Figure 19:
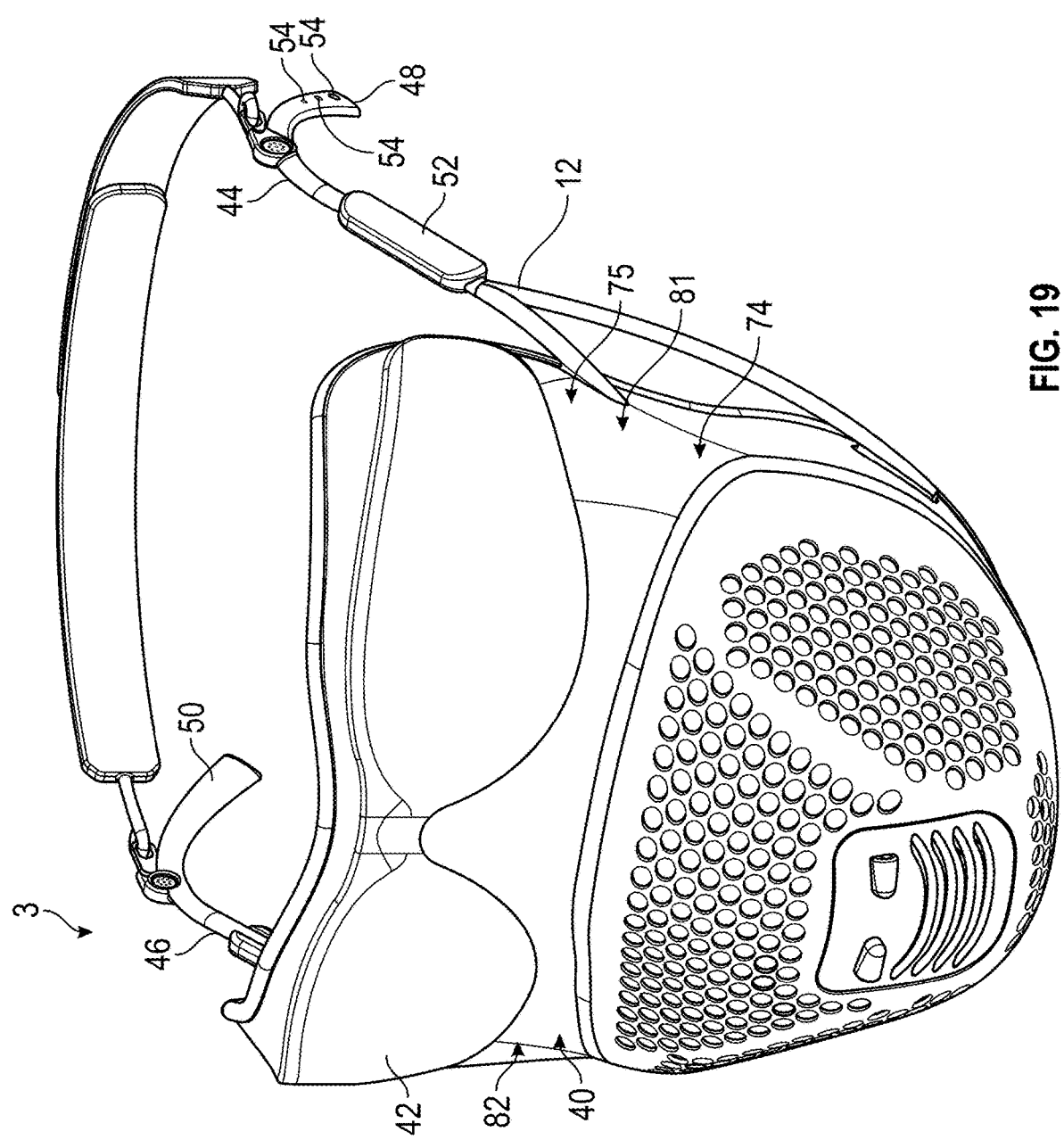
FIG. 19 is a front perspective view of an example of a third embodiment of a protection device having a filter assembly that is structured to cover a user's nose and mouth and to form a first sealed compartment that encloses the user's nose and mouth, and having an upper portion that includes a skirt that extends to an eye shield, the upper portion structured to form a second sealed compartment around the user's eyes, where in various examples the protective device can also include one or more other features, including for example, a microphone, earpieces, and/or other communication circuits, and UV-C light emitting diodes (LEDs).
Figure 20:
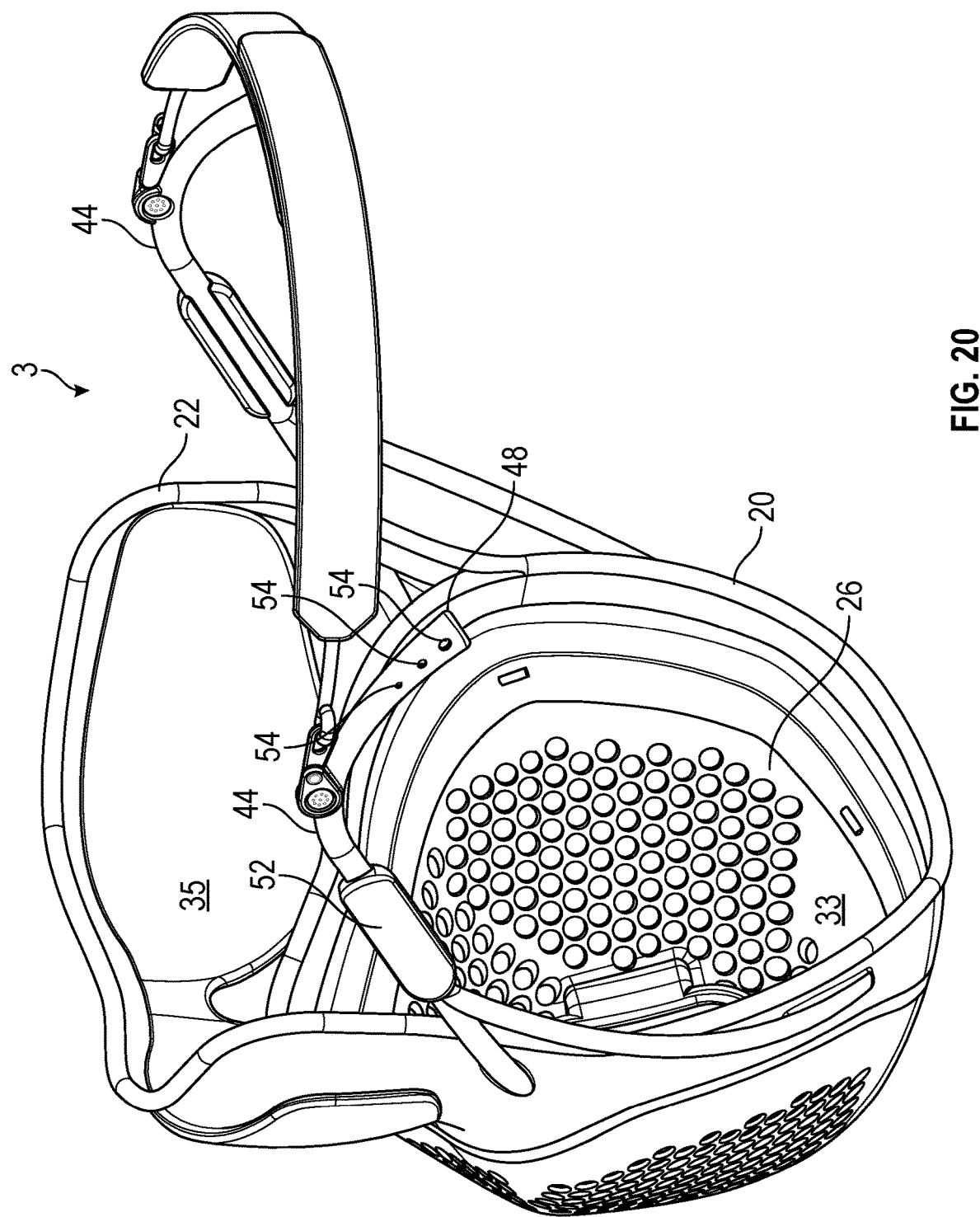
FIG. 20 is a back perspective view of the protection device illustrated in FIG. 19.
Figure 21:
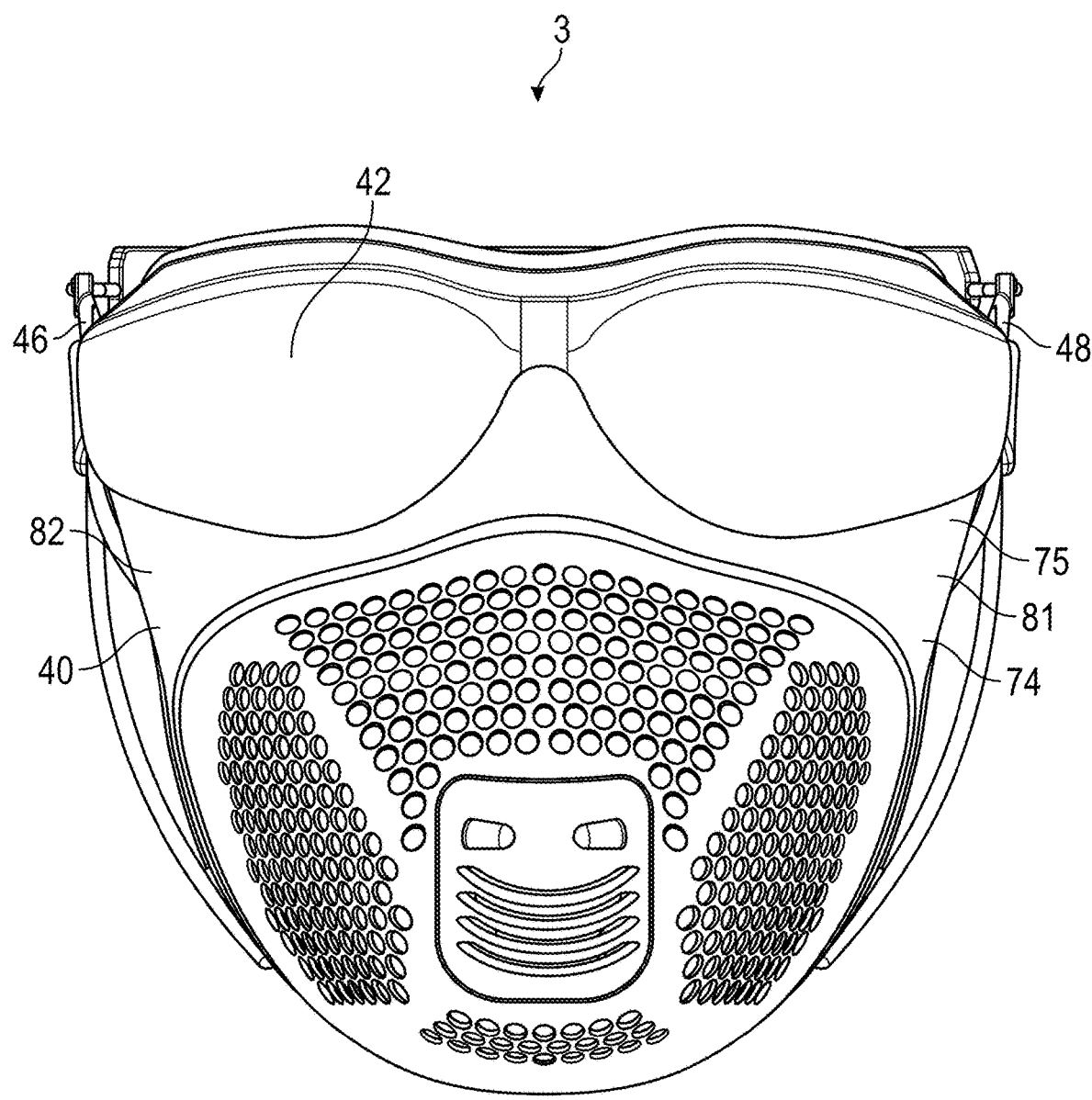
FIG. 21 is a front view of the embodiment of the protection device illustrated in FIG. 19.
Figure 22:
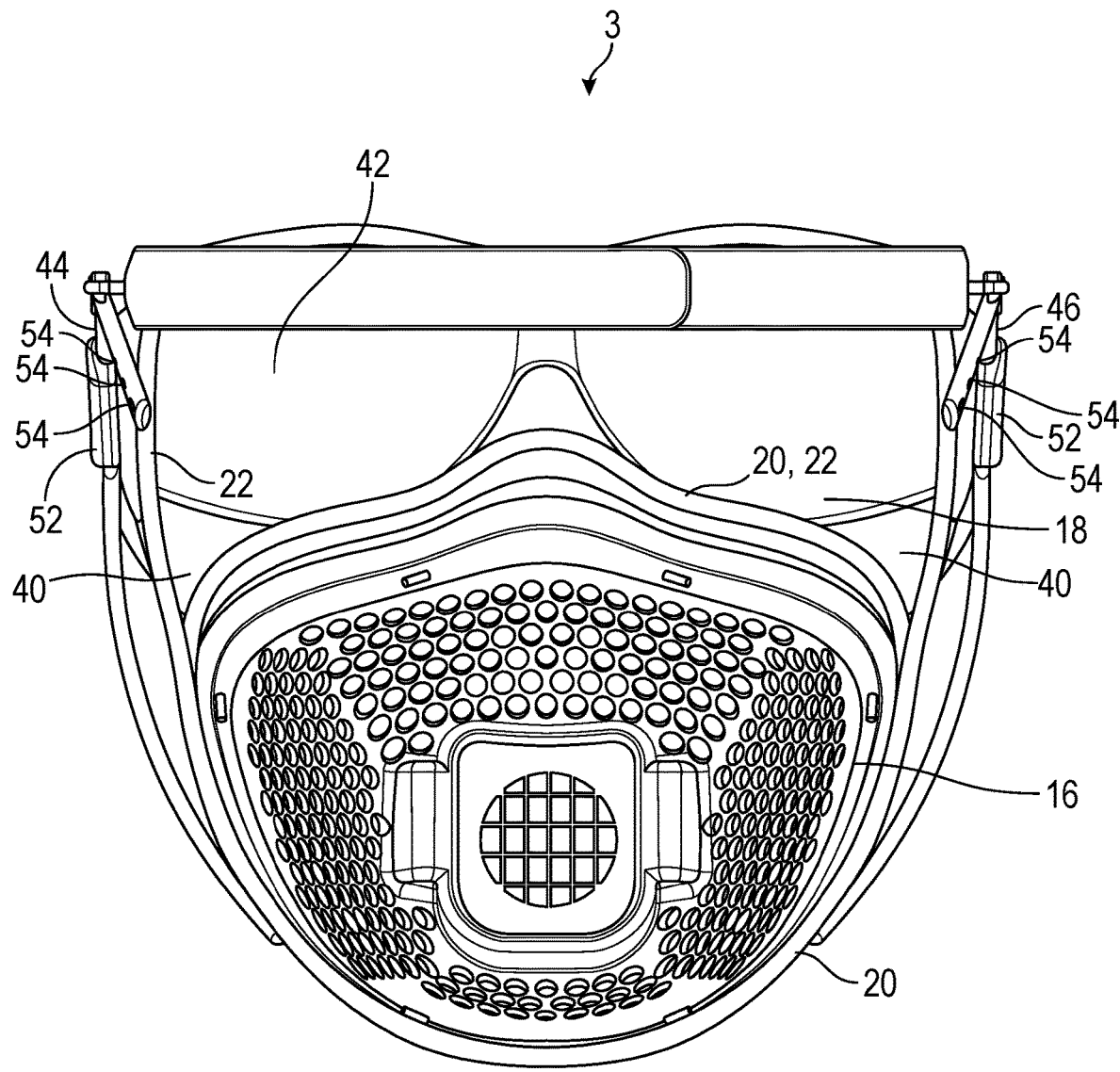
FIG. 22 is a back view of the embodiment of the protection device illustrated in FIG. 19.
Figure 23:
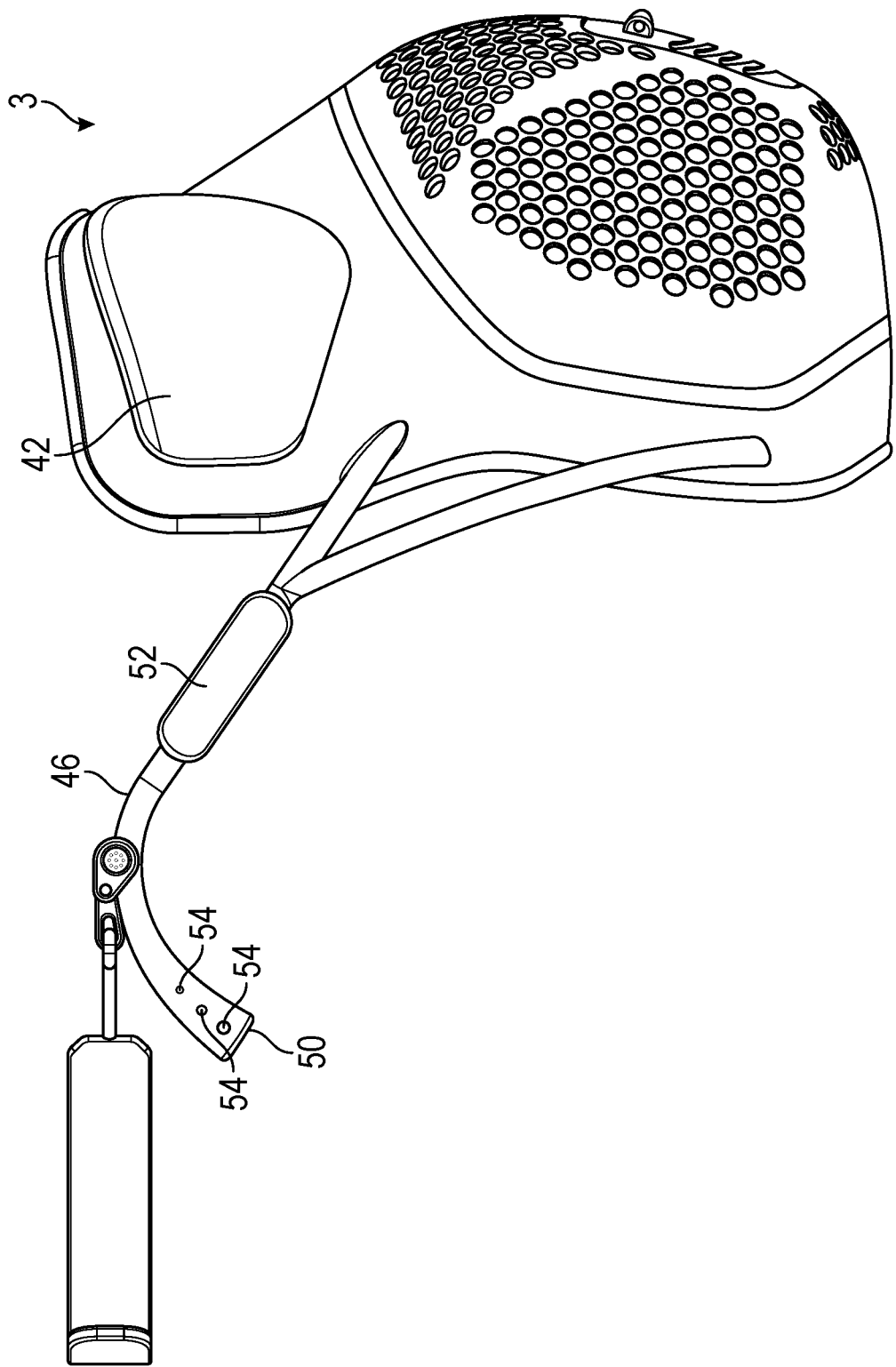
FIG. 23 is a right-side view of the embodiment of the protection device illustrated in FIG. 19.
Figure 24:
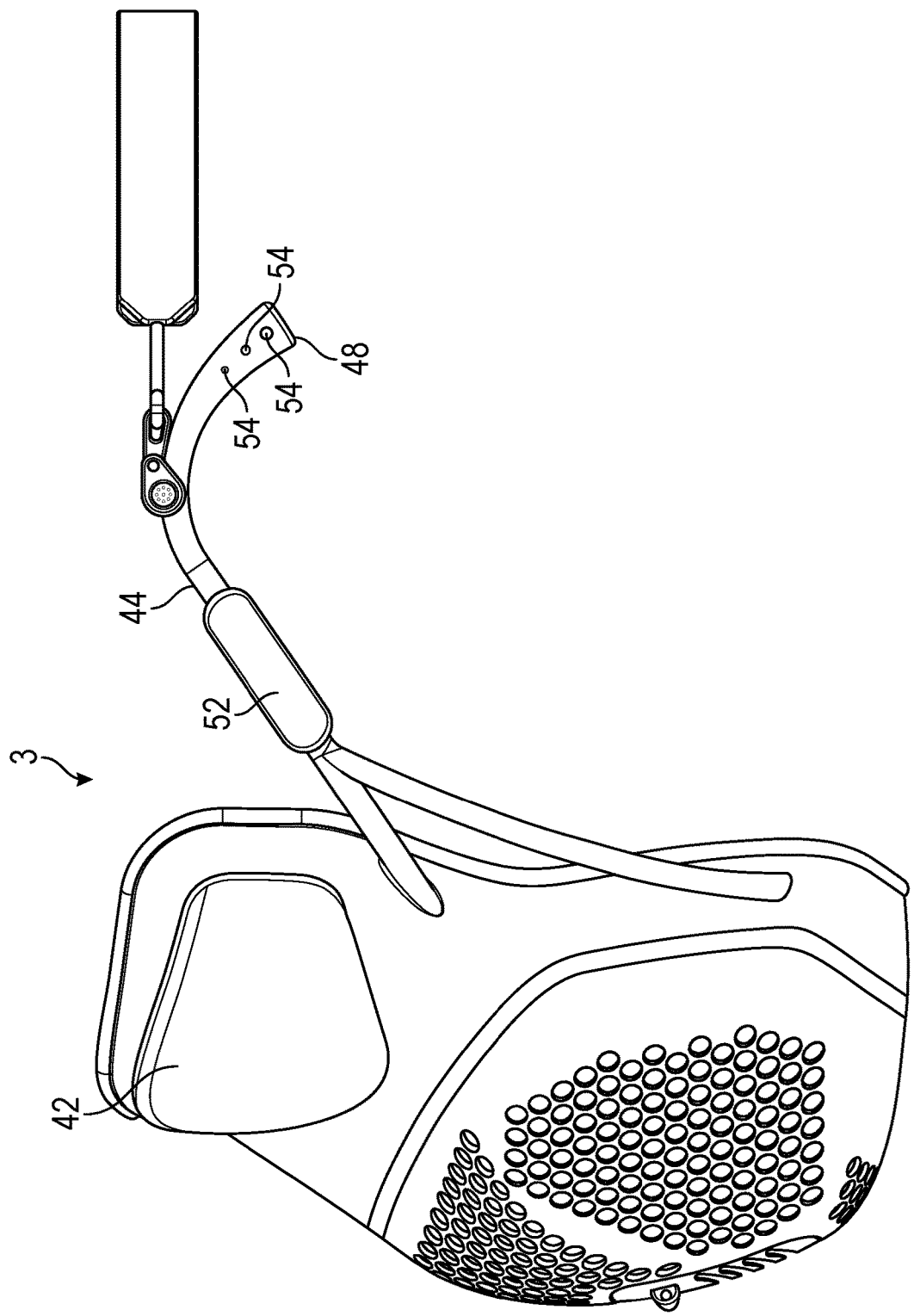
FIG. 24 is a left-side view of the embodiment of the protection device illustrated in FIG. 19.
Figure 25:
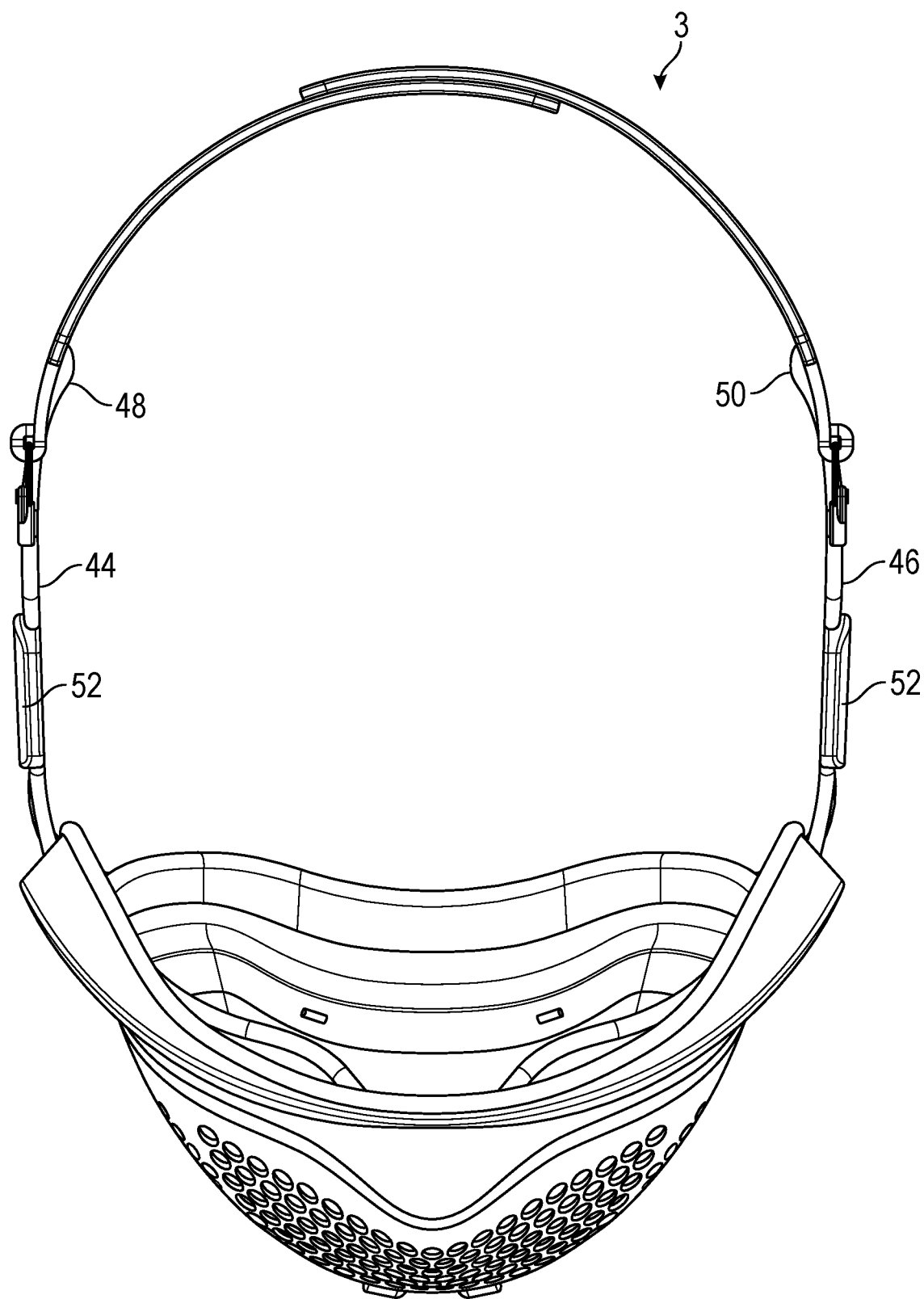
FIG. 25 is a top view of the embodiment of the protection device illustrated in FIG. 19.

FIG. 19 is a front perspective view of an example of a third embodiment of a protection device 3 having a filter assembly 5 that is structured to surround and cover a user's nose and mouth to protect inhalation and ingestion of undesired material, and to form a sealed compartment 16 that encloses the user's nose and mouth. Device 3 also has an upper portion that includes a skirt 40 that extends to an eye shield 42. As described in further detail below, the seal 14 includes a first seal 20 positioned along the edges of a first compartment, and a second seal 22 positioned along the edges of a second safety compartment 18 that is structured to cover and surround a user's eyes. Device 3 is described in reference to FIGS. 19-27 which illustrate the example of the third embodiment, where FIG. 19 is a front perspective view, FIG. 20 is a back perspective view, FIG. 21 is a front view, FIG. 22 is a back view, FIG. 23 is a right-side view, FIG. 24 is a left-side view, FIG. 25 is a top view, and FIG. 26 is a bottom view. FIG. 27 is an exploded view of this example of the third embodiment and illustrates certain features and characteristics that may not be able to be seen in FIGS. 19-27. Note, for clarity of the illustrations, all of the corresponding depictions of certain features in each of FIGS. 19-27 may not be enumerated even though they illustrate different views of the same feature. Protection device 3 may have many structural features that are the same or similar to features of protection device 1 (as illustrated in FIGS. 1-9 and described above in reference to protection device 1) and device 2 (as illustrated in FIGS. 10-18 and described above in reference to protection device 2). For example, the filter assembly 5, the valve 38, the temple arms 44, 46, left and right brace 68, 71, the ear supports 48, 50, microphone 56, speakers 54, communication circuit 52, strap 66, eye shield 42, skirt 40, etc., and the description of any similar features of devices 1 and 2 applies to device 3 as well. Protection device 3 also has some different structural features that are different as discussed below.

Protection device 3 also includes a skirt 40 that extends from the filter assembly 5 to an eye shield 42. In various embodiment, the skirt 40 can be a rigid, semi-rigid or a pliable material. An upper portion of the skirt 40 is coupled to a lower portion of the eye shield 42 along a bottom edge of the eye shield 42 forming a protective barrier that covers the portion of a user's face between their mouth and nose, and their eyes. The skirt 40 of protection device 3 differs from the skirt of protection device 2 in that in device 3, the skirt 40 extends further to the left and right on the device such that when worn, the skirt 40 extends further around the user's head. Also, the skirt 40 extends around the eye shield 42 to a back edge of the device 3, to seal 14. In this embodiment, the upper portion of the device 3 includes a second safety compartment 18 that encloses a second volume 35. A portion of seal 14, second seal 22, is positioned along a peripheral proximal edge of the second safety compartment 18. The second safety compartment 18 is shaped to be placed over the eyes of a user, enclosing a user's eyes with the second seal positioned against the user's face. When the device 3 is worn, the first safety compartment 16 and the second safety compartment 18 enclose the user's mouth/nose and eyes (respectively) simultaneously, providing protection from inhaling undesired material and protection from exposing eyes to undesired material.

FIG. 28 illustrates an example of a side view of a device 200 that is configured to be coupled to a filter for attaching the filter to a user's face. Such devices include, for example, a rigid or a semi-rigid frame that can include two arm assemblies 201 (e.g., a left arm assembly and a right arm assembly). Each arm assembly 201 can be attached to one side of a filter (e.g., the left side and right side) and hold the filter therebetween. When worn by a user, each arm assembly 201 extends along one side of the user's head, the proximal (front) end 220 of the arm assembly 201 coupled to the filter and the distal (back) end 222 of the arm assembly 201 supported by the user's ear. Each arm assembly 201 can look similar, or identical. FIG. 28 illustrates an example of an arm assembly 201 that can be a left arm assembly or a right arm assembly. In some embodiments, a portion of the device 200, or the entire device 200 is formed from a transparent material.

The arm assembly 201 includes a temple arm 202 that is adapted to fit alongside of a user's head, for example, to be positioned adjacent to a user's temple. The temple arm 202 can be structured like the temple arms 44, 46 described in reference to devices 1-3 above. The temple arm 202 may be referred to a right and left temple arm in reference to the side of a user's head the temple arm is configured to be positioned adjacent to.

Such devices can also include one or more support structures 204 that extend from a portion of a temple arm 202 and provide rigidity and support for holding a filter tight against a user's face. The support structures 204 can be formed from a stretchable rubber or a non-latex material, or can be rigid or semi-rigid. In some embodiments, the support structures are configured similar to the left brace 68 and the right brace 71 described above in reference to protection devices 1-3. In some embodiments, a frame can be coupled to each of the left and right arm assemblies and can fully encircle a filter attached to the device 200, or partially encircle the filter. In some embodiments, the filter can include a valve that is bias closed, and configured to allow carbon dioxide exhaled from a user to be expelled from the device through the valve.

Each arm assembly 201 can be coupled to a filter at one or more attachment points. Each arm assembly 201 can comprise a first fastener 208 positioned on a proximal end 220 of the temple arm 202. Each arm assembly 202 can also include a second fastener 210 at the distal end 213 of a brace 204. In use, for a right-side arm assembly, the first fastener 208 is attached to an upper side portion of the filter on the right side of a filter, and the second fastener 210 is attached to a lower portion of the filter on the right side of the filter. For the left-side arm assembly, the first fastener 208 is attached to an upper side portion of the filter on the left side of a filter, and the second fastener 210 is attached to a lower portion of the filter on the left side of the filter. The right and left arm assemblies are place on the respective sides of a user's head, with the ear supports contacting the user's ears to hold the device 200 and attached filter to the user's head. In some embodiments, one or more cross-members extends between the left and right arm assemblies and are coupled to the arm assemblies to provide connection between the arm assemblies and increase the rigidity of the device 200 holding a filter. In some embodiments, all or part of the arm assemblies comprises a stretchable material.

In some embodiments, at least one fastener comprises a clamp. In some embodiments, the clamp comprises a spring. In some embodiments, at least one fastener comprises Velcro. In some embodiments, at least one fastener comprises an adhesive. In some embodiments, at least one fastener comprises a staple. In some embodiments, at least one fastener comprises a snap. In some embodiments, at least one fastener comprises a button. In some embodiments, at least one fastener comprises rubber or plastic. In some embodiments, at least one fastener comprises a material with a low melting point, such that the material can be heated and adhered to filter. In some embodiments, the at least one fastener attaches to a filter using a corresponding coupling structure on the filter. For example, the fastener may include an elongated cylindrical member that fits into a corresponding cylindrical receptacle on the mask. In some embodiments, one or more portions of the frame comprise a slot which is shaped and sized such that a portion of a filter can be placed inside the slot and held in place. For example, the proximal end of the temple arms may each comprise a slot. In some examples, slot may be 0.1-25 mm long. The slot may have a cross-sectional area that is slightly smaller than the thickness of a filter material such that the filter material may be pushed into the slot and held in place by friction. In some embodiments, the slot includes one or more teeth or other protruding structures that are configured to contact a portion of the filter placed in the slot and hold the filter in place in the slot. In some embodiments, other portions of the frame include such slots. For example, the lower end of the first support and the second support may also include a slot (or another type of fastener).

In some embodiments, an arm assembly 201 comprises a rigid or semi rigid plastic. In some embodiments, the arm assembly comprises an elastomeric material. In some embodiments, at least one of the first or second temple arms 202 comprises an ear support 206 having curved portion configured to be positioned behind the ear of a user when the user is wearing the device. In some embodiments, the device 200 includes a communication circuit, for example, a wireless transceiver. In some embodiments, at least one arm assembly 201 comprises an earpiece 212 configured to produce sound. In some embodiments, the device 200 further comprises a wireless receiver coupled to the ear piece. In some embodiments, the wireless receiver is configured to use a Bluetooth protocol for communication. In other examples, any other wireless protocol may be used. In some embodiments, the device 200 further comprises a receiver with a wired connection coupled to the earpiece such that the receiver can be attached by the wired connection to a computer, a cell phone, and the like.

In some embodiments, the device 200 further includes a filter coupled to the frame. The filter is configured to prevent airborne material from passing through the filter. In some embodiments, the filter is configured to prevent 90% of airborne solid particles from passing through the filter. In some embodiments, the filter is configured to prevent about 91%, 92%, 93%, 94%, 95%, 96%, 97%, 98%, 99%, or more than 99% (+/−05%), of airborne solid particles from passing through the filter.

Another innovation includes a method of preventing inhalation of undesired material, the method comprising providing a device 200 having a frame for holding a filter, the frame including a first temple arm having a fastener configured to be coupled to a portion of a filter, a second temple arm having a fastener configured to be coupled to a portion of the filter, a first support having a first end coupled to the first temple arm and a second end having a fastener configured to be coupled to a portion of the filter, and a second support having a first end coupled to the second temple arm and a second end having a fastener configured to be coupled to a portion of the filter, coupling a filter to the first temple arm, the second temple arm, the first support, and the second support, and positioning the device on the head of a user such that the filter covers the user's nose and mouth, and the first temple arm is positioned adjacent to the user's right temple and the second temple arm is positioned adjacent to the user's left temple.

Another innovation includes a device 200, comprising a frame for holding a filter, the frame including a first temple arm having a proximal end and a distal end, the first temple arm including a fastener positioned on the proximal end for coupling the first temple arm to a filter, the distal end structured to be positioned alongside a temple of a user wearing the device, a second temple arm having a proximal end and a distal end, the second temple arm including a fastener positioned on the proximal end for coupling the second temple arm to a filter, the distal end structured to be positioned alongside a temple of a user wearing the device, and a first support having a first end coupled to the first temple arm and a second end including a fastener configured for coupling the first support to a portion of the filter, and a second support having a first end coupled to the second temple arm and a second end including a fastener configured for coupling the second support to a portion of the filter.

In some embodiments, the fasteners are releasably attachable to the filter. In some embodiments, the device further includes a filter coupled to the first temple arm, the second temple arm, the first support, and the second support. In some embodiments, the frame further comprises a bridge structure connecting the proximal end of the first temple arm to the proximal end of the second temple arm. In some embodiments, the frame further comprises a lower member coupled to the second end of the first support and the second end of the second support. In some embodiments, the frame further comprises a lower member coupled to the second end of the first support and the second end of the second support, a first side member coupled to the proximal end of the first temple arm and coupled to the lower end of the first support, and a second side member coupled to the proximal end of the second temple arm and coupled to the lower end of the second support.

Implementation Consideration

The foregoing description details certain embodiments of the systems, devices, and methods disclosed herein. It will be appreciated, however, that no matter how detailed the foregoing appears in text, the systems, devices, and methods can be practiced in many ways. As is also stated above, it should be noted that the use of particular terminology when describing certain features or aspects of the invention should not be taken to imply that the terminology is being re-defined herein to be restricted to including any specific characteristics of the features or aspects of the technology with which that terminology is associated.

Conditional language such as, among others, "can," "could," "might" or "may," unless specifically stated otherwise, are otherwise understood within the context as used in general to convey that certain embodiments include, while other embodiments do not include, certain features, elements and/or steps. Thus, such conditional language is not generally intended to imply that features, elements and/or steps are in any way required for one or more embodiments or that one or more embodiments necessarily include logic for deciding, with or without user input or prompting, whether these features, elements and/or steps are included or are to be performed in any particular embodiment.

Headings are included herein for reference and to aid in locating various sections. These headings are not intended to limit the scope of the concepts described with respect thereto. Such concepts may have applicability throughout the entire specification.

Many variations and modifications may be made to the above-described embodiments, the elements of which are to be understood as being among other acceptable examples. All such modifications and variations are intended to be included herein within the scope of this disclosure. The foregoing description details certain embodiments. It will be appreciated, however, that no matter how detailed the foregoing appears in text, the systems and methods can be practiced in many ways. As is also stated above, it should be noted that the use of particular terminology when describing certain features or aspects of the systems and methods should not be taken to imply that the terminology is being re-defined herein to be restricted to including any specific characteristics of the features or aspects of the systems and methods with which that terminology is associated.

It will also be understood that, when a feature or element (for example, a structural feature or element) is referred to as being "connected", "attached" or "coupled" to another feature or element, it may be directly connected, attached or coupled to the other feature or element or intervening features or elements may be present. In contrast, when a feature or element is referred to as being "directly connected", "directly attached" or "directly coupled" to another feature or element, there may be no intervening features or elements present. Although described or shown with respect to one embodiment, the features and elements so described or shown may apply to other embodiments. It will also be appreciated by those of skill in the art that references to a structure or feature that is disposed "adjacent" another feature may have portions that overlap or underlie the adjacent feature.

Terminology used herein is for the purpose of describing particular embodiments and implementations only and is not intended to be limiting. For example, as used herein, the singular forms "a", "an" and "the" may be intended to include the plural forms as well, unless the context clearly indicates otherwise. It will be further understood that the terms "comprises" and/or "comprising," when used in this specification, specify the presence of stated features, steps, operations, processes, functions, elements, and/or components, but do not preclude the presence or addition of one or more other features, steps, operations, processes, functions, elements, components, and/or groups thereof. As used herein, the term "and/or" includes any and all combinations of one or more of the associated listed items and may be abbreviated as "/".

In the descriptions above and in the claims, phrases such as "at least one of" or "one or more of" may occur followed by a conjunctive list of elements or features. The term "and/or" may also occur in a list of two or more elements or features. Unless otherwise implicitly or explicitly contradicted by the context in which it used, such a phrase is intended to mean any of the listed elements or features individually or any of the recited elements or features in combination with any of the other recited elements or features. For example, the phrases "at least one of A and B;" "one or more of A and B;" and "A and/or B" are each intended to mean "A alone, B alone, or A and B together." A similar interpretation is also intended for lists including three or more items. For example, the phrases "at least one of A, B, and C;" "one or more of A, B, and C;" and "A, B, and/or C" are each intended to mean "A alone, B alone, C alone, A and B together, A and C together, B and C together, or A and B and C together." Use of the term "based on," above and in the claims is intended to mean, "based at least in part on," such that an unrecited feature or element is also permissible.

Spatially relative terms, such as "forward", "rearward", "under", "below", "lower", "over", "upper" and the like, may be used herein for ease of description to describe one element or feature's relationship to another element(s) or feature(s) as illustrated in the figures. It will be understood that the spatially relative terms are intended to encompass different orientations of the device in use or operation in addition to the orientation depicted in the figures. For example, if a device in the figures is inverted, elements described as "under" or "beneath" other elements or features would then be oriented "over" the other elements or features due to the inverted state. Thus, the term "under" may encompass both an orientation of over and under, depending on the point of reference or orientation. The device may be otherwise oriented (rotated 90 degrees or at other orientations) and the spatially relative descriptors used herein interpreted accordingly. Similarly, the terms "upwardly", "downwardly", "vertical", "horizontal" and the like may be used herein for the purpose of explanation only unless specifically indicated otherwise.

As used herein in the specification and claims, including as used in the examples and unless otherwise expressly specified, all numbers may be read as if prefaced by the word "about" or "approximately," even if the term does not expressly appear. The phrase "about" or "approximately" may be used when describing magnitude and/or position to indicate that the value and/or position described is within a reasonable expected range of values and/or positions. For example, a numeric value may have a value that is +/−0.1% of the stated value (or range of values), +/−1% of the stated value (or range of values), +/−2% of the stated value (or range of values), +/−5% of the stated value (or range of values), +/−10% of the stated value (or range of values), etc. Any numerical values given herein should also be understood to include about or approximately that value, unless the context indicates otherwise.

For example, if the value "10" is disclosed, then "about 10" is also disclosed. Any numerical range recited herein is intended to include all sub-ranges subsumed therein. It is also understood that when a value is disclosed that "less than or equal to" the value, "greater than or equal to the value" and possible ranges between values are also disclosed, as appropriately understood by the skilled artisan. For example, if the value "X" is disclosed the "less than or equal to X" as well as "greater than or equal to X" (e.g., where X is a numerical value) is also disclosed. It is also understood that the throughout the application, data is provided in a number of different formats, and that this data, may represent endpoints or starting points, and ranges for any combination of the data points. For example, if a particular data point "10" and a particular data point "15" may be disclosed, it is understood that greater than, greater than or equal to, less than, less than or equal to, and equal to 10 and 15 may be considered disclosed as well as between 10 and 15. It is also understood that each unit between two particular units may be also disclosed. For example, if 10 and 15 may be disclosed, then 11, 12, 13, and 14 may be also disclosed.

Although various illustrative embodiments have been disclosed, any of a number of changes may be made to various embodiments without departing from the teachings herein. For example, the order in which various described method steps are performed may be changed or reconfigured in different or alternative embodiments, and in other embodiments one or more method steps may be skipped altogether. Optional or desirable features of various device and system embodiments may be included in some embodiments and not in others. Therefore, the foregoing description is provided primarily for the purpose of example and should not be interpreted to limit the scope of the claims and specific embodiments or particular details or features disclosed.

The examples and illustrations included herein show, by way of illustration and not of limitation, specific embodiments in which the disclosed subject matter may be practiced. As mentioned, other embodiments may be utilized and derived therefrom, such that structural and logical substitutions and changes may be made without departing from the scope of this disclosure. Such embodiments of the disclosed subject matter may be referred to herein individually or collectively by the term "invention" merely for convenience and without intending to voluntarily limit the scope of this application to any single invention or inventive concept, if more than one is, in fact, disclosed. Thus, although specific embodiments have been illustrated and described herein, any arrangement calculated to achieve an intended, practical or disclosed purpose, whether explicitly stated or implied, may be substituted for the specific embodiments shown. This disclosure is intended to cover any and all adaptations or variations of various embodiments. Combinations of the above embodiments, and other embodiments not specifically described herein, will be apparent to those of skill in the art upon reviewing the above description.

The disclosed subject matter has been provided here with reference to one or more features or embodiments. Those skilled in the art will recognize and appreciate that, despite of the detailed nature of the example embodiments provided here, changes and modifications may be applied to said embodiments without limiting or departing from the generally intended scope. These and various other adaptations and combinations of the embodiments provided here are within the scope of the disclosed subject matter as defined by the disclosed elements and features and their full set of equivalents.

What is claimed is:

1. A protection device, comprising:
    a filter assembly having a proximal side for positioning near the face of a user and a distal side, the filter assembly comprising:
        a filter;
        a proximal layer and a distal layer, the proximal layer and the distal layer each having a plurality of perforations that allow air to pass through, the filter assembly configured to hold the filter between the proximal layer and the distal layer;
    a one-way valve positioned in a center portion of the filter assembly and coupled to the proximal layer of the filter assembly, the valve configured to allow air to pass through the valve from the proximal side of the filter assembly to the distal side of the filter assembly;
    a frame assembly coupled to the filter assembly and structured to attach the protection device to the head of the user, the frame assembly comprising:
        a left temple arm having a proximal end coupled to the filter assembly; and
        a right temple arm having a proximal end coupled to the filter assembly;
    a seal positioned along a peripheral edge of the filter assembly, the filter assembly and the seal defining a first safety compartment for enclosing a user's mouth and nose;
    an eye shield assembly having a proximal side and a distal side, and the eye shield assembly forming an upper portion of the protection device, the eye shield assembly comprising
        an optically transparent eye shield, wherein the seal is further positioned along a peripheral edge of the eye shield, the eye shield and the seal defining a second safety compartment for enclosing the user's eyes, wherein the first safety compartment is separate from the second safety compartment when worn by the user such that air cannot flow between the first safety compartment and the second safety compartment;

a skirt coupling the eye shield to the filter assembly and positioned distal to the seal, wherein the seal is further positioned along a left peripheral edge and a right peripheral edge of the skirt, the skirt comprising a semi-rigid or rigid material, and forming a protective barrier extending between the filter assembly and the eye shield for covering a portion of the face of the user, the left temple arm and the right temple arm extending from the skirt; and the frame assembly further comprising:

a left temple arm brace coupled to the left temple arm and extending towards a lower portion of the filter assembly and coupled to the filter assembly and a right temple arm brace coupled to the right temple arm and extending towards the lower portion of the filter assembly and coupled to the filter assembly.

2. The protection device of claim 1, further comprising a visible communication circuit.

3. The protection device of claim 2, wherein the communication circuit includes a battery.

4. The protection device of claim 2, wherein the communication circuit includes a microphone and speakers.

5. The protection device of claim 4, wherein the microphone is configured to be positioned near the mouth of the user.

6. The protection device of claim 2, wherein the communication circuit is configured to communicate with another device via a wired or wireless connection.

7. The protection device of claim 4, wherein the speakers are positioned in the left temple arm and right temple arm.

8. The protection device of claim 1, wherein the filter includes a proximal surface and a distal surface, and wherein the protection device further comprises a UV-C light emitting diode (LED) positioned to emit UV-C radiation on a portion of the distal surface of the filter.

9. The protection device of claim 1, wherein the filter includes a proximal surface and a distal surface, and wherein the protection device further comprises two or more UV-C light emitting diodes (LED's) positioned to emit UV-C radiation on a portion of the distal surface of the filter that is on the left and right side of the one-way valve.

10. The protection device of claim 9, wherein the two UV-C LED's are a first set of LED's and are coupled to the one-way valve.

11. The protection device of claim 10, further comprising a second set of one or more UC-V LED's coupled to the one-way valve, the second set of one or more UV-C LED's positioned to emit light on an outer surface of the distal layer of the filter assembly.

12. The protection device of claim 11, wherein the second set of one or more UV-C LED's includes two UV-C LED's.

13. The protection device of claim 1, wherein the proximal and distal layer each comprise a plurality of openings arranged in a pattern.

14. The protection device of claim 1, wherein the distal layer and the filter are removably attachable to the filter assembly, the one-way valve is coupled to the proximal layer of the filter assembly, and the filter includes an opening shaped and sized to fit closely around the one-way valve when the filter is sandwiched between the distal layer and the proximal layer of the filter assembly.

15. The protection device of claim 14, wherein the distal layer and the proximal layer include corresponding and aligned fasteners positioned along peripheral edges of the distal and proximal layers for coupling the distal layer to the proximal layer.

16. The protection device of claim 1, wherein the device further comprises a safety strap connected to the left temple arm and the right temple arm for positioning behind the head of the user.

17. The protection device of claim 1, wherein the seal comprises pliable rubber, silicon, or a non-latex material that allows the seal to conform to the face of the user and provide an airtight seal of the first safety compartment along the peripheral edge of the first safety compartment.

18. The protection device of claim 1, wherein the filter assembly and the eye shield assembly including the skirt comprise a transparent material.

* * * * *